(12) United States Patent
McKenzie et al.

(10) Patent No.: US 6,177,256 B1
(45) Date of Patent: Jan. 23, 2001

(54) ANTIGEN CARBOHYDRATE COMPOUNDS AND THEIR USE IN IMMUNOTHERAPY

(75) Inventors: Ian F. C. McKenzie; Vasso Apostolopoulos; Geoff Allan Pietersz, all of Victoria (AU)

(73) Assignee: Austin Research Institute, Victoria (AU)

( * ) Notice: Under 35 U.S.C. 154(b), the term of this patent shall be extended for 0 days.

(21) Appl. No.: 09/223,043

(22) Filed: Dec. 30, 1998

Related U.S. Application Data

(63) Continuation of application No. 08/833,807, filed on Apr. 9, 1997, now Pat. No. 5,989,552, which is a continuation of application No. 08/340,711, filed on Nov. 16, 1994, now abandoned.

(30) Foreign Application Priority Data

Dec. 26, 1993 (AU) .......................................................... 3223

(51) Int. Cl.[7] ........................ G01N 33/574; A61K 39/00; A61K 39/385; C07K 1/00

(52) U.S. Cl. .................. 435/7.23; 424/185.1; 424/193.1; 424/194.1; 424/196.11; 424/197.11; 424/198.1; 530/395

(58) Field of Search ........................ 435/7.23; 424/185.1, 424/193.1, 196.1, 196.11, 197.11, 198.1; 530/395

(56) References Cited

PUBLICATIONS

IDS references of the parent application 08/340,711 were reviewed.*

* cited by examiner

*Primary Examiner*—Hankyel Park
(74) *Attorney, Agent, or Firm*—Dann Dorfman Herrell and Skillman, P.C.

(57) ABSTRACT

Conjugates between one or more repeated subunits of an antigen and a carbohydrate polymer are desired. Also described are immunogenic vaccines against disease states which contain the conjugates and methods for inducing cell-mediated immune responses. The conjugates may especially contain polymers of the carbohydrate mannose and one or more repeated subunits of human mucin.

16 Claims, 10 Drawing Sheets

Tumor challenge with 10 6 cells

Figure 1:
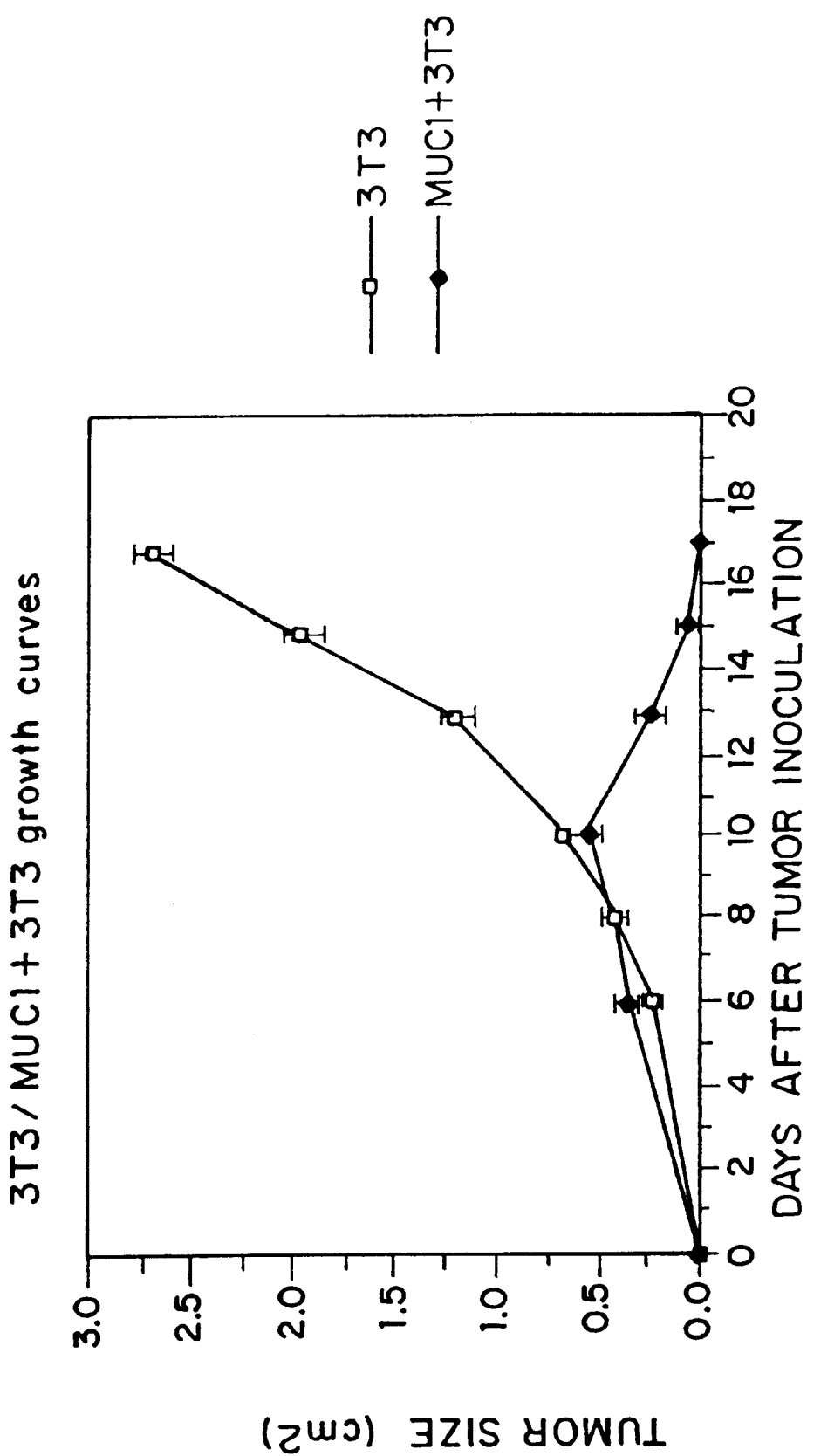

MICE IMMUNIZED WITH:
- □ Mannan
- ◆ Mannan+FP
- ○ Mannan-FP
- ■ PBS

- △ M16.IFP
- ● Oxid Man
- ■ PBS
- ○ MFP

- □ DEP
- ● PBS
- ■ MFP

ANTIGEN CARBOHYDRATE COMPOUNDS AND THEIR USE IN IMMUNOTHERAPY

This application is a continuation of U.S. application Ser. No. 08/833,807, filed Apr. 9, 1997, now U.S. Pat. No. 5,989,552, which is a continuation of U.S. application Ser. No. 08/340,711, filed Nov. 16, 1994, abandoned.

This invention relates to the immunotherapy of disease states, and in particular, but not exclusively to the immunotherapy of carcinomas.

Cancer is a major cause of death and severe trauma in modern society. Cancer is no respecter of persons as the young, old, males, females and peoples of all races may contract cancer, although cancer in children is relatively rare, perhaps with the exception of childhood leukemia. In western society, cancer of the colon and lung cancer are major diseases. In women, breast cancer is the most common form of cancer.

Many cancers are accompanied by overproduction of human mucin. Mucins are heavily glycosylated proteins (greater than about 100 Kd) which are produced by many epithelial cells and tumours (1). Mucins found on cancer cells are different in some respects to those on normal epithelial cells, in that some mucins have a deficiency in their carbohydrate coat which leaves the protein core exposed. (2). There are seven forms of known human mucin designated MUC1, MUC2, MUC3, MUC4, MUC5 MUC6 and MUC7 (3, 4, 26, 27). MUC1 is the most ubiquitous. The various mucins all have very similar properties, that is, they are transmembrane glycoproteins, all having a variable number of repeated amino acid sequences, which have a high content of serine, threonine and proline. Overproduction of aberrantly glycosylated mucins (either non-glycosylated or a deficiency in glycosylation) is characteristic of tumours of the breast, ovary, pancreas, colon, lungs, prostate and other tumours of secretory tissue. The cDNA sequences of the respective protein cores of the human mucins MUC1 to MUC7 have been cloned and characterized and have been found to contain highly repetitive central portions of varying numbers of repeats of particularly amino acid motifs (known as VNTR's). By way of example, MUC1 consists of unique amino and carboxyl terminal sequences separated by a highly repetitive central portion containing forty to eighty tandemly arranged copies or repeats of a twenty amino acid motif. The VNTR's of MUC1 through MUC7 are set forth below:

MUC1 VNTR (SEQ ID NO:1)—SAPDTRPAPGSTAPPAHGVT
MUC2 VNTR (SEQ ID NO:2)—PTTTPISTTTMVTPTPTPTGTQT
MUC3 VNTR (SEQ ID NO:3)—HSTPSFTSSITTTETTS
MUC4 VNTR (SEQ ID NO:4)—TSSASTGHATPLPVTD
MUC5 VNTR (SEQ ID NO:5)—PTTSTTSA (494 base pair insert—eight amino acid tandem repeat)
MUC6 VNTR—169aa repeat unit
MUC7 VNTR (SEQ ID NO:6)—TTAAPPTPPATTPAPPSSSAPPE The repeated subunit of MUC6 comprises 169 amino acids, although at this time the amino acid sequence of this repeat unit has not been fully characterized. The MUC7 sequence has recently been published (27).

Finn and colleagues have demonstrated that in the lymph nodes of patients with breast cancer (5, 6), cancer of the pancreas, ovary and other tumours, cytotoxic lymphocytes are present which react with human mucin. Antibodies to the MUC1 peptide can block the activity of these cytotoxic T-lymphocytes on MUC1$^+$ target cells (5, 6). Recently, cytotoxic lymphocytes to a murine lung cancer have also been described (28).

The surgery associated with tumour removal is traumatic to the patient, often disfiguring, and costly. Established chemotherapeutic and radiation procedures for tumour treatment which may be carried out in place of or in conjunction with surgical procedures are often debilitating and associated with severe side-effects. There is accordingly an urgent need for therapeutic compounds and methods for the prevention/treatment of tumours.

There is an urgent need for new compounds and methods for the treatment of cancer. Similarly, there is a pressing need for alternative compounds and therapies for the treatment of other disease states such as type I allergies, malaria, HIV, dental caries, flu, cholera, foot and mouth disease, meningitis, Leishmania infection, whooping cough, rabies, Streptococcus infection, respiratory infection, measles, Lyme disease, tuberculosis, bacterial meningitis, shingles, rubella, hepatitis, herpes, hepatitis A, polio, venereal disease/trachoma, hepatitis B, common cold, cervical cancer, meningitis/pneumonitis, chicken pox, small pox, pneumonia/PUO.

In accordance with the first aspect of the present invention, there is provided a compound comprising a conjugate between an antigen and a carbohydrate polymer.

In accordance with another aspect of the present invention, there is provided a compound comprising a conjugate between the human mucin polypeptide, one or more repeated subunits thereof, or a fragment of said repeated subunits, with a carbohydrate polymer.

In a preferred embodiment of the present invention, the carbohydrate polymer is a polymer of the carbohydrate mannose.

Insofar as the present invention is concerned, the antigen can be a human autoantigen or a peptide antigen derived from a virus, microorganism or plant or an amino acid subunit of at least five amino acids in length of a human autoantigen or a peptide antigen derived from a virus, microorganism or plant. The antigen of the present invention can also consist of more than one, five or more amino acid subunits (as mentioned above) linked together. These linked subunits may be from the same or different origins within the bounds described above.

Examples of the antigens envisaged by the present invention are as follows: pollens, hepatitis C virus (HIV) core, E1, E2 and NS2 proteins, Plasmodium faliciparum circumsporozoite protein, HIV-gp120/160 envelope glycoprotein, streptococcus surface protein Ag, influenza nucleoprotein, haemagglutinin-neuraminidase surface infection, TcpA pilin subunit, VP1 protein, LMCV nucleoprotein, Leishmania major surface glycoprotein (gp63), Bordetella pertussis surface protein, rabies virus G protein, Streptococcus M protein, Syncyticial virus (RSV) F or G proteins, Epstein Barr virus (EBV) gp340 or nucleoantigen 3A, haemagglutinin, Borrelia burgdorferi outer surface protein (Osp) A, Mycobacterium tuberculosis 38 kDa lipoprotein or Ag85, Neisseria meningitidis class 1 outer protein, Varicella zoster virus IE62 and gpI, Rubella virus capsid protein, Hepatitis B virus pre S1 ag, Herpes simplex virus type I glycoprotein G or gp D or CP27, Murray valley encephalitis virus E glycoprotein, Hepatitis A virus VP1, polio virus capsid protein VP1, VP2 and VP3, chlamydia trachomatis surface protein, Hepatitis B virus envelope Ag pre S2, Human rhinovirus (HRV) capsid, papillomavirus peptides from oncogene E6 and E7, Listeria surface protein, Varicella virus envelope protein, Vaccinia virus envelope protein, Brucella surface protein, a combination of one or more of said antigens, an amino acid subunit of said antigens comprising five or more amino acids in length or combinations of one or more of said subunits.

The antigens of the present invention can also consist of whole cells or sub-cellular fractions thereof. Such cells or sub-cellular fractions thereof may be derived from any tumour type or other source. Examples of cancer types from which the whole cells or sub-cellular fractions may be derived are breast, lung, pancreas and colon cancer and melanoma. Some further examples of specific antigens obtained from tumours are melanoma specific antigen (for example, the MAGE series antigen), carcino embryonic antigen (CEA) from colon and other cancers or indeed antigens extracted from any tumour.

This invention includes any one or more of the antigens listed and in particular includes any one ore more of the human mucins MUC1 through MUC7 which, as mentioned above, all comprise highly repetitive central portions of repeated amino acid sequences which are high in serine, threonine and proline. In particular, the compounds of this invention may comprise a human mucin polypeptide (containing a variable number of repeats associated with normal allelic variation), or may comprise one or more of the repeated sequences of human mucin, preferably two to eighty, more preferably two to twenty and even more preferably two to ten repeated subunits of human mucin. The human mucin and subunits thereof are preferably non-glycosylated or aberrantly glycosylated so as to provoke an immune response to the mucins found on cancer cells which have a deficiency in their carbohydrate coat which leaves the protein core exposed. The use of human mucin MUC1 is particularly preferred although it is to be clearly understood that the invention extends to the use of any antigen and especially to the use of the human mucins MUC1 through MUC7. For the purpose of convenience, the term MUC will hereafter be used to refer to any of the human mucins MUC1 through MUC6 and repeated subunits thereof. While only the human mucins will be dealt with hereafter, it must be kept in mind that his invention equally relates to any other antigen as mentioned previously.

Fragments of MUC may also be conjugated to a carbohydrate polymer. These fragments would generally comprise from five to twenty amino acids from the repeated amino acid sequences of any of mucins MUC1 through MUC6. For example, a fragment of the mucin MUC1 may comprise the amino acid sequence APDTR, APDTRPAPG, DTRPAPGSTAPP, and the like (see SEQ ID NO:1). For convenience of description these fragments are also included with the definition MUC. Similarly, other antigen fragments comprising at least five amino acids may be conjugated to a carbohydrate polymer.

A specified antigen (such as MUC1, MUC2, MUC3, MUC4, MUC5, MUC6 or MUC7) may form part of a fusion protein in order to facilitate expression and purification on production of the fusion protein in recombinant host cells. The non-antigen portion of the fusion protein would generally represent the N-terminal region of the fusion polypeptide with the carboxy terminal sequences comprising antigen sequences. Fusion proteins may be selected from glutathione-S-transferase, β-galactosidase, or any other protein or part thereof, particularly those which enable affinity purification utilizing the binding or other affinity characteristics of the protein to purify the resultant fusion protein. The protein may also be fused to the C-terminal or N-terminal of the carrier protein. The nature of the fusion protein will depend upon the vector system in which fusion proteins are produced. An example of a bacterial expression vector is pGEX which on subcloning on a gene of interest into this vector produces a fusion protein consisting of glutathione-S-transferase with the protein of interest. Examples of other vector systems which give rise to fusion proteins with a protein of interest are described in Sambrook et al (7), which is incorporated herein in its entirety by reference. These can be included or cleaved; if included they could a have a "carrier" function.

The protein or fusion protein maybe expressed in a number of prokaryotic (*E.coli* or β-sutilis) or eukaryotic (baculovirus, CHO cells, cos cells or yeast) expression systems. In some of these systems, for example, baculovirus or yeast, by introducing glycosylation motifs into the protein or fusion protein, the mannose rich glycosylation may be adequate; negating the need for chemically linking with mannose rich carbohydrate polymers. These novel fusion proteins may be used with or without mild periodate oxidation.

The carbohydrate portion of the compounds of the invention may comprise any carbohydrate polymer, for example, selected from polymers of glucose, galactose, mannose, xylose, arabinose, fucose, glucosamine, galactosamine, rhamnose, 6-0-methyl-D-galactose, 2-0-acetyl-β-D-xylose, N-acetyl-glucosamine, iduronate, guluronate, mannuronate, methyl galacturonate, α-D-galactopyranose 6-sulphate, fructose and α abequose, conformation and configuration isomers thereof, or a carbohydrate formed of two or more different monomer units. The number of repeated monomer units in the polymer is not important but generally carbohydrate polymers would comprise at least twenty monomer units, preferably in excess of one hundred monomer units, more preferably in excess of one thousand monomer units, and still more preferably in excess of ten thousand monomer units or more. Carbohydrate polymers may be a mixture of polysaccharide chains of varying molecular weights. Most preferably the carbohydrate polymer is a polymer of mannose or is a carbohydrate polymer containing mannose units.

Antigens may be conjugated to a carbohydrate polymer according to standard processes well known in the art of carbohydrate chemistry for the derivatization and reaction of polysaccharides and monosaccharides. Carbohydrates may be oxidized with conventional oxidizing reagents such as sodium periodate to give a polyaldehyde which is then directly reacted with the antigen (such as repeated subunits of MUC1) where amino functional groups on the protein chain (such as the ε group of lysine) react with the aldehyde groups which may optionally be further reduced to form a Schiff base. Polysaccharide chains may be first activated with cyanogen bromide and the activated polysaccharide then reacted with a diamine, followed by conjugation to the antigen to form a conjugate which may optionally then be oxidized. The carbohydrate and polypeptide may be derivatized with bifunctional agents in order to cross-link the carbohydrate and polypeptide. Commonly used cross-linking agents include 1,1-bis(diazoacetyl)-2-phenylethane, glutaraldehyde, N-hydroxysuccinimide esters, for example, esters with 4-azidosalicyclic acid, homobifunctional imidoesters including disuccinimidyl esters such as 3,3'-dithiobis(succinimidyl-propionate), and bifunctional maleimides such as bis-N-maleimido-1,8-octane. Derivatizing agents such as methyl-3-[(p-azido-phenyl)dithio] propioimidate yield photactivitable intermediates which are capable of forming cross-links in the presence of light. Oxidized carbohydrates may be reacted with hydrazine derivatives of antigens to give a conjugate. Alternatively, carbohydrates may be reacted with reagents such as carbonyl diimidazole, which after oxidation gives the desired conjugate.

The coupling of antigens to a carbohydrate involves converting any or all of the functional groups on the carbohydrate to reactive groups and thereafter reacting the reactive groups on the carbohydrate with reactive groups on the polypeptide. Carbohydrate polymers are replete with hydroxide groups, and in some instances, carboxyl groups (such as in idruionate), ester groups (such as methylgalacturonate) and the like. These groups may be activated according to standard chemical procedures. For example, hydroxyl groups may be reacted with hydrogen halides, such as hydrogen iodide, hydrogen bromide and hydrogen chloride to give the reactive halogenated polysaccharide. Hydroxy groups may be activated with phosphorous trihalides, active metals (such as sodium ethoxide, aluminium isopropoxide and potassium tert-butoxide), or esterified (with groups such as tosyl chloride or acetic acid) to form reactive groups which can be then be reacted with reactive groups on the polypeptide to form one or more bonds. Other functional groups on carbohydrates apart from hydroxyl groups may be activated to give reactive groups according to well known procedures in the art.

Polypeptides comprising MUC or other antigens may be produced according to well known procedures such as peptide synthesis, protein purification, or expression of polypeptides in host cells. Peptide synthesis may be employed for polypeptides containing up to about a hundred amino acids (for example, five repeated subunits of MUC1). Generally, for polypeptide containing about twenty or more amino acids, the preferred means of production is recombinant expression in a host cell, preferably a prokaryotic host cell, and more preferably a bacterial host cell. However, as discussed earlier, eukaryotic systems may also be used. Procedures for expression of recombinant proteins in host cells are well established, see, for example, Sambrook, et al (7).

Carbohydrates may be purified from natural sources or synthesized according to conventional procedures. Carbohydrates are available commercially from many suppliers.

In another aspect, the invention relates to an immunogenic vaccine against human disease states and in particular against tumour cells expressing human mucin or a subunit thereof, which comprises a compound comprising a conjugate between an antigen and a carbohydrate polymer, in association with a pharmaceutically acceptable carrier. Antigens which may be used in this aspect of the invention are as previously described. The vaccine is administered to human patients to protect against various disease states including cancer cell growth, and in particular, the growth of tumours of secretory tissues, such as tumours of the breast, colon, lung, pancreas, prostate, and the like. Patients may be immunized with the vaccine to protect against tumour formation of secretory tissues. Alternatively, patients suffering from tumours may be immunized with the vaccine as part of a therapeutic regimen for tumour treatment. By way of example, to protect women from breast cancer, women may be immunized with the vaccine pre- or post-puberty and may receive one-or more injections, preferably an initial immunization, followed by one or more booster injections separated by several months to several years. In one immunization schedule, women may be immunized with the compounds of the invention and then receive a booster immunization at appropriate intervals. Further booster immunizations are then provided at regular intervals. The route of immunization is no different from conventional human vaccine administration. Accordingly, vaccines may be administered subcutaneously, intramuscularly, orally, intravenously, and the like.

Some other disease states which may be protected against in this manner include, type I allergies, malaria, HIV, dental caries, flu, cholera, foot and mouth disease, meningitis, Leishmania infection, whooping cough, rabies, Streptococcus infection, respiratory infection, measles, Lyme disease, tuberculosis, bacterial meningitis, shingles, rubella, hepatitis, herpes, hepatitis A, polio, venereal disease/trachoma, hepatitis B, common cold, cervical cancer, meningitis/pneumonitis, chicken pox, small pox, pneumonia/PUO.

The amount of compounds of the invention or compositions thereof delivered to a patient is not critical or limiting. An effective amount of a compound of the invention is that which will stimulate an immune response against the antigen component. The amount of compounds or compositions delivered may vary according to the immune status of the patient (depending on whether the patient is immunosuppressed or immunostimulated), the judgement of attending physician or veterinarian whether the compound is used as a vaccine to prevent or treat a disease state or as a vaccine to prevent tumour formation, or whether the vaccine is used in the treatment of an existing tumour. By way of example, patients may receive from 1 $\mu$g to 10,000 $\mu$g of the compounds of the invention, more preferably 50 $\mu$g to 5,000 $\mu$g, still more preferably 100 $\mu$g to 1,000 $\mu$g, and even more preferably 100 $\mu$g to 500 $\mu$g of the compounds of the invention. Adjuvants are not generally required. However, adjuvants may be used for immunization. Suitable adjuvants include alum, as well as any other adjuvant or adjuvants well known in the vaccine art for administration to humans.

Compounds of the invention may be administered to patients in concert with a cytokine or other immune regulator. By way of example, immune regulators which may be administered in concert with the compounds of the invention include one or more of GM-CSF, G-CSF, M-CSF, TNF$\alpha$ or $\beta$, interferon $\alpha$ or $\gamma$, any of IL1 through IL13, or any other cytokine. The immune regulator may be administered at the same time as the compounds of the invention, optionally as part of a multi-component administration form. Alternatively, the compounds of this invention and immune regulators may be administered at different time intervals.

In a still further aspect of this invention, there is provided a method for inducing a cell mediated immune response against antigens which comprises administering to an animal (including a human) a compound comprising a conjugate between said antigen and a carbohydrate polymer, optionally in association with a pharmaceutically acceptable carrier.

The immunization of humans and animals with the compounds of this invention may provoke a potentiated cellular response of activated T-lymphocytes which are cytotoxic to cells expressing the antigen component. By way of example, humans and animals may be immunized against tumours which express human mucins. A potential benefit of this invention arises from the fact that animals may be protected against cancer prior to tumour growth, as the compounds of the invention may provoke a cellular immune response of cytotoxic T-cells which kill tumour cells expressing mucin or other antigenic determinants. This invention is applicable to the immunization against tumours of secretory tissue, such as adenocarcinomas, more particularly, tumours of the breast, ovary, pancreas, colon, lung, prostate and the like.

The compounds of the invention may also be used as therapeutic agents for the treatment of patients suffering from cancer, as a part of the overall treatment for eradication of the cancer. Thus, the compounds of the invention may be administered to patients suffering from cancer either before or after surgery to remove the tumour. Preferably the compounds are administered as part of a chemotherapeutic regime following tumour excision. In these circumstances, the compounds of the invention are administered in amounts consonant with standard chemotherapeutic regimes for the administration of cytotoxic compounds for use in tumour treatment.

The compounds of this invention can also be used in immunization for therapy or prophylaxis of other disease states as mentioned earlier.

In a still further aspect, the invention relates to the use of a compound comprising a conjugate between the human mucin polypeptide, one or more repeated subunits thereof, or a fragment of said repeated subunits and a carbohydrate polymer in the treatment of adenocarcinoma, particularly breast cancer.

The compounds of this invention possess the advantage of being substantially non-toxic on administration to animals or humans, and as a consequence the compounds are well tolerated by administration to patients.

The invention described herein is not restricted to the human mucin MUC1. The invention clearly extends to the use of other mucins expressed by cancer cells, as well as to the use of other antigens which on coupling to polysaccharides, can be used to provoke cytotoxic T-cell responses against tumour cells, which compounds may be used in vaccines to prevent tumour formation, as well as for the treatment of cancer, and/or the treatment or prophylaxis of other disease states as mentioned earlier.

The invention will now be described with reference to the following non-limiting Examples.

The following abbreviations are used in the Examples:
Abbreviations
ELISA: enzyme linked immunosorbent assay
DTH: delayed type hypersensitivity
FP: fusion protein
GST: glutathione-S-transferase
HMFG: human milk fat globule
Kd: kilodalton
KLH: keyhole-limpet haemocyanin
PAGE: polyacrylamide gel electrophoresis
PBS: phosphate buffered saline
SDS: sodium dodecyl sulphate
Tc: cytotoxic T-lymphocytes
VNTR: variable number of tandem repeats
CTL: cytotoxic T-cells
M-FP: mannan fusion protein
MHC: major histocompatability complex
MSA: mucin serum antigen
CASA: circulating MUC1 serum antigen

FIGURE LEGEND

FIG. 1: Growth of $5 \times 10^6$ 3T3 and MUC1$^+$3T3 cells is BALB/c mice.

Figure 2A:
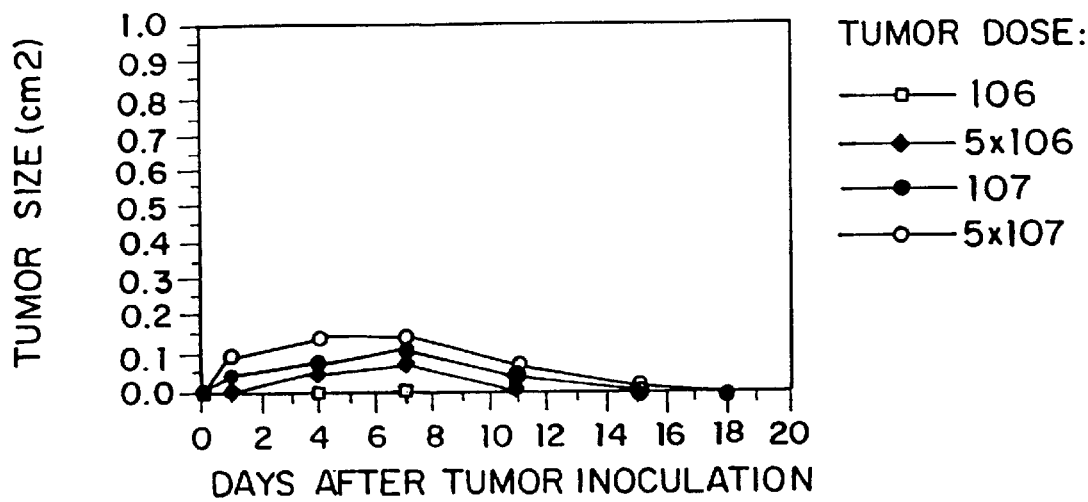

FIG. 2: Dose response of MUC1$^+$3T3 cells in (a) mannan-fusion protein and (b) non immunized BALB/c mice. Doses ranging from $10^6$–$5 \times 10^7$ cells.

FIG. 3: Mice immunized with (a) mannan, mixture of mannan+fusion protein, M-FP and a control group (immunized with PBS); (b) 16.1FP-mannan, oxidized mannan, pure M-FP, M-FP and PBS; (c) dextran-FP (D-FP), M-FP and PBS, and challenged with $10^6$ MUC1$^+$3T3 cells.

Figure 4:
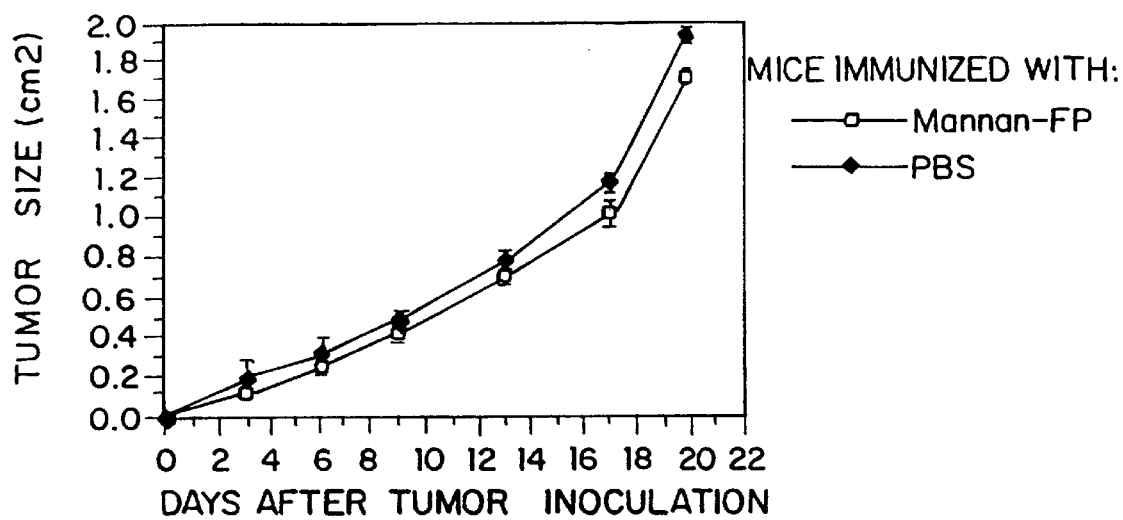

FIG. 4: Mice immunized with M-FP protein and a control group immunized with phosphate buffer and challenged with $10^6$ 3T3 cells.

Figure 5:
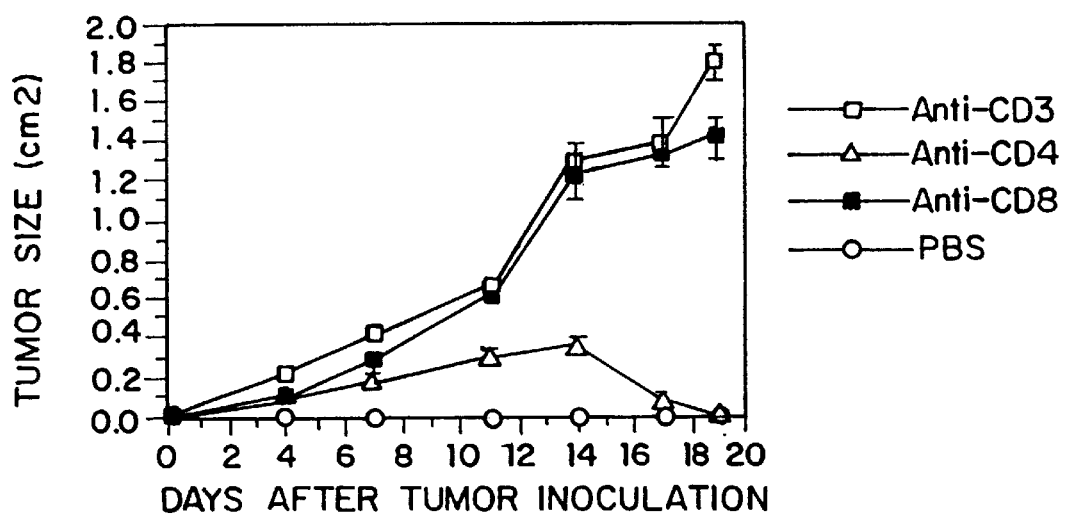

FIG. 5: BALB/c mice treated with anti-CD3, anti-CD4 and anti-CD8 on −2, 0, +2 days. Challenge with $10^6$ MUC1$^+$ 3T3 cells.

Figure 6:
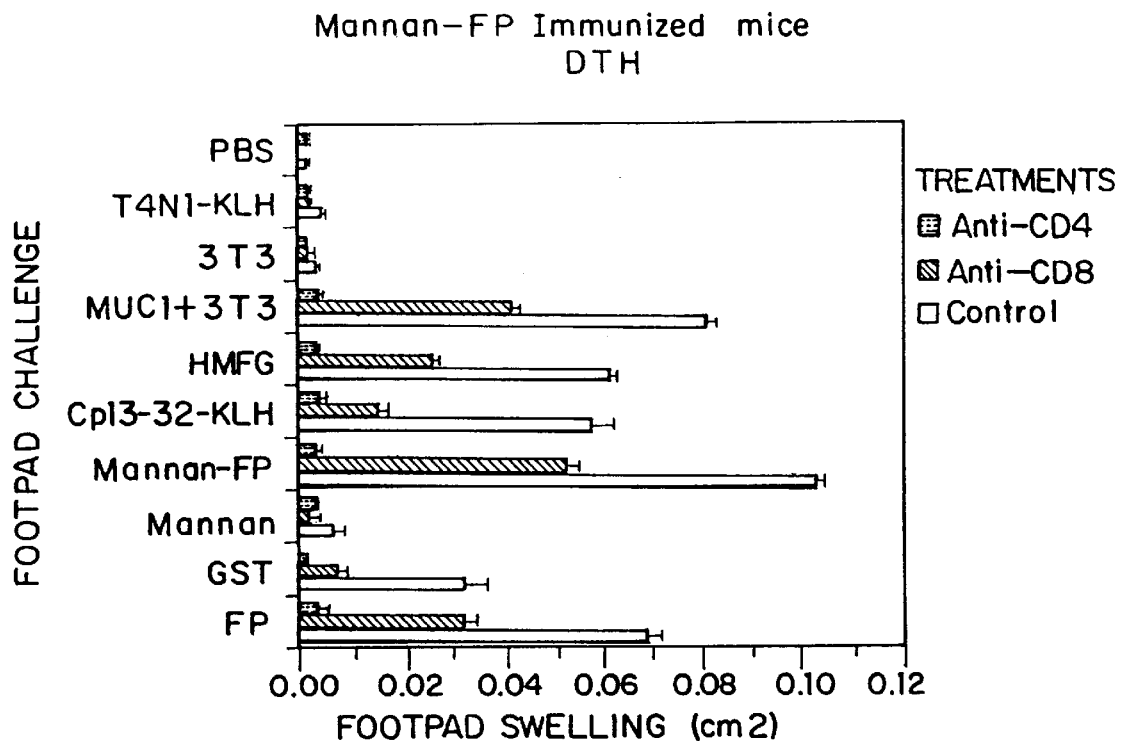

FIG. 6: DTH response measured at forty-eight hours in mice immunized with mannan-fusion protein and challenged with dead 3T3 and MUC1$^+$3T3 cells, Cp13-32-KLH, fusion protein, HMFG, mannan-fusion protein, GST, T4N1 and PBS in their hind footpads. Control (black box), mice treated with anti-CD4 (grey box) and mice treated with anti-CD8 (cross lines).

Figure 7:
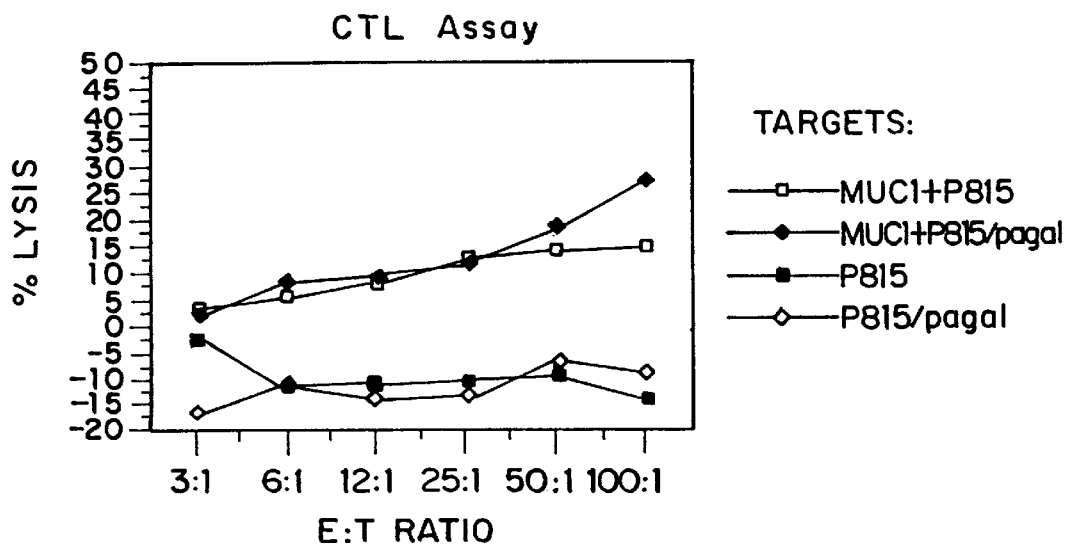

FIG. 7: Cytotoxic T-lymphocyte assay with P815±pagal and MUC1$^+$P815±pagal treated target cells.

FIG. 8: A: (DBA2$^{++}$×BALB/c)F1 mice were challenged with $5 \times 10^6$ MUC1$^+$P815 cells. After thirteen days of tumour challenge (established tumours) mice were immunized with 5 μg M-FP (5 μg corresponding to the amount of FP) once or every other day. Control mice were injected with PBS;

B: DBA/2$^{++}$ mice were challenged with $5 \times 10^6$ MUC1$^+$ P815 cells. After fifteen days of tumour challenge (established tumours) mice were immunized with 5 μg M-FP (5 μg corresponding to the amount of FP) once or every other day. Control mice were injected with PBS.

FIG. 9: A, B and C—the figures show the level of mammary serum antigen (MSA) in the serum of patients. The vertical axis gives the level (unity/ml) according to the manufacturer's instructions, the horizontal axis refers to different patients.

A: dose (0.15 mg) patients 1,2 and 3;
B: dose (0.25 mg) patients 1 to 4;
C: dose (0.5 mg) patients 1 to 3.

FIG. 10: A, B and C—the figures show the level of cancer associated serum antigen (CASA) in the serum of patients. The vertical axis gives the level (immunity/ml) according to the manufacturer's instructions, the horizontal refers to different patients.

A: dose (0.15 mg) patients 1, 2 and 3;
B: dose (0.25 mg) patients 1 to 4;
C: dose (0.5 mg) patients 1 to 3.

FIG. 11: A, B, C, D and E—the figures show the antibody titres (measured as OD=optical density) in ELISA assays to different antigens.

A: anti-FP=fusion protein;
B: anti-DT=diphtheria toxoid;
C: anti-HMFG=human milk fat globular proteins;
D: anti-Cp13 to 32=anti-MUC1 peptide;
E: =anti-STPA (control, non-reactive peptide).

The groups are as in the preceding figures. That is,
group 1=0.15 mg peptide injected,
group 2=0.25 mg peptide injected,
group 3=0.05 mg peptide injected,
and the numbers are the patients (in this case 1 to 10). The bar code is shown on the figure for each patient injected before and at times after immunizations.

EXAMPLE 1

Materials and Methods
Synthetic Peptides, Fusion Protein, and HMFG Production and Immunization Peptides C-p13–32 (MUC1 VNTR), p31–55 and p51–70 (N-terminal to VNTR) and p344–364 and p408–423 (C-terminal to VNTR) were synthesized using an Applied Biosystems Model 430A automated peptide synthesizer (sequences shown in Table 1). The mouse CD4 N-terminal region peptide (T4N1) was also synthesized and used as a negative control peptide (Table 1). HMFG, was isolated from human milk (8). A fusion protein (9) containing 5

VNTR repeats was produced by subcloning the cDNA into the bacterial expression vector pGEX-3X (10) (Table 1).

BALB/c mice (females aged eight weeks) were immunized intraperitoneally with 50 µg of either fusion protein, HMFG, C-p13–32 (coupled to diphtheria-toxoid with glutaraldehyde) or T4N1 (coupled to diphtheria toxoid) emulsified in complete Freund's adjuvant and this was repeated four and six weeks later in phosphate buffered saline. Prior to tumour injection and after tumour rejection mice were bled and the serum was tested on an ELISA for antibody production against the relevant immunogens.

MUC1$^+$3T3 tumour injections (see later description for production of these cells) were given subcutaneously in 0.2 mls containing the appropriate tumour dose. Mice treated with anti-CD3, anti-CD4, anti-CD8 and anti-γ-interferon antibodies were given three intraperitoneal injections of 0.2 mls on days −2, 0 and +2 (0=day of tumour injection). Mice to be treated with antibody were injected subcutaneously with the tumour on day zero and on day five (tumour size approximately 0.15 cm$^2$) when they were treated with rabbit complement (fresh serum —0.2 mls intravenously) and antibody (0.2 mls intraperitoneally), on days five and seven.

containing the soluble FP was mixed with glutathione-agarose beads (sulphur-linked) (Sigma, St. Louis) and collected by centrifugation. The FP ((C-PAHGVTSAPDTRPAPGSTAP)×5-GST) was eluted with buffer containing 5 mM reduced glutathione, dialyzed against phosphate buffered saline and analysed by SDS-PAGE.

Polyacrylamide gel electrophoresis: Samples to be tested were mixed with SDS sample buffer, boiled for five minutes and then loaded onto a 12.5% SDS-PAGE gel. Gels were stained in 0.2% Coomasie blue and then destained in 7% acetic acid or were silver stained (16). Molecular weight markers used: 200, 000 myosin; 116, 000 β-galactosidase; 92, 500 phosphorylase b: 66, 200 Bovine serum albumin; 43, 000 Hen egg white ovalbumin; 31,000 Bovine carbonic anhydrase; 21,500, Soybean trypsin inhibitor, and 14,400 Hen egg white lysozyme.

Conjugation of Mannan to MUC1 Fusion Protein

Mannan was oxidized to a poly-aldehyde by treating 14 mg of mannan (a mannose containing polysaccharide) in 1 ml of 0.1M phosphate buffer pH6.0 to pH9.0 with 100 µl 0.1M sodium periodate in phosphate buffer for one hour at

TABLE 1

Sequences of synthetic peptides

| Peptide | Amino Acid Sequence |
|---|---|
| MUC1 VNTR: Cp-13–32 (SEQ ID NO: 7) | C-PAHGVTSAPDTRPAPGSTAP |
| Fusion protein (SEQ ID NO: 8) | (PAHGVTSAPDTRPAPGSTAP) × 5-GST |
| N-terminal region to MUC1: | |
| p31–55 (SEQ ID NO: 9) | TGSGHASSTPGGEKETSATQRSSVP |
| p51–70 (SEQ ID NO: 10) | RSSVPSSTEKNAVSMTSSVL |
| C-terminal to MUC1: | |
| p334–364 (SEQ ID NO: 11) | NSSLEDPSTDVVQELQRDISE |
| p408–423 (SEQ ID NO: 12) | TGFNQYKTEAASRVNL |
| Mouse CD4: T4N1 (SEQ ID NO: 13) | KTLVLGKEQESAELPCEY |

Treatment of Mice with Antibodies

To ensure that the antibodies to CD3, CD4 and CD8 were depleting or blocking CD3$^+$, CD4$^+$ and CD8$^+$ T-cells, a serological analysis of residual cells was performed using the antibodies to CD3, CD4 and CD8. Spleen and lymph node cells were removed from normal and treated BALB/c mice, the lymphocytes were teased, washed in DME and incubated at 37° C. for five minutes in 0.83% ammonium chloride to lyse red blood cells. Serology tests were performed where 2×10$^5$ spleen/lymph node cells from mice were added to a 1:500 dilution of anti-CD3, anti-CD4 and anti-CD8 ascites. Following extensive washing, the cells were incubated with (mouse thymus cell absorbed) rat anti-mouse IgG and incubated for thirty minutes on ice. Mice which had been treated with anti-CD3, anti-CD4, anti-CD8 or anti-CD4+CD8 were each tested with these antibodies. It was found that the CD3$^+$ cells were depleted and CD4$^+$ and CD8$^+$ cells had been blocked.

Preparation of Soluble GST-MUC1 Fusion Protein

A 309 base pair insert (PDF9.3) encoding a little more than 5 repeats of a 60 base pair motif from the VNTR region of MUC1 cDNA (10) was subcloned into the bacterial expression vector pGEX-3X, in the correct reading frame and orientation (11). Fusion protein (FP), consisting of glutathione-S-transferase (GST, 26 Kd) and MUC1 VNTR (12 Kd), was induced with 0.1 mM IPTG (11). Cells were collected by centrifugation, washed and lysed by sonication in buffer containing 1% (v/v) Triton X-100. Supernatant 4° C. Following a further 30 minute incubation at 4° C. with 10 µl ethandiol, the mixture was passed through a PD-10 column and the mannan fraction collected; 230 µg of MUC1 FP was added to the oxidized mannan, reacted overnight at room temperature and used for subsequent studies.

The fusion protein was radiolabelled with 125$_I$ using chloramine-T. The unlabelled fusion protein was mixed with radiolabelled fusion protein such that the specific activity was 1×10$^7$ cpm/µg and reacted with oxidized mannan as above. The mannan-FP was stabilized by reducing the Schiffs bases and residual aldehyde groups. The complex was then analysed by SDA-PAGE, Western blot analysis and by gel permeation chromatography using sepharyl S-208 column (1.5 cm×100 cm).

Immunization Schedule

BALB/c mice (females aged eight weeks) were immunized intraperitoneally with 5 µg (corresponding to amount of FP) mannan-FP, FP and a mixture of non-conjugated mannan+FP in phosphate buffered saline (PBS) once weekly for three weeks. Mice were previously immunized with FP alone and this was used for a control for antibody production (see below). Prior to tumour injection, mice were bled and the serum tested by ELISA (see below) for antibody production against FP, (anti-mannan antibodies).

Tumours and Antibodies

The BALB/c mouse fibroblast cell line 3T3 transfected with the MUC1 cDNA transmembrane form with the ras gene and a cell line MUC1$^+$3T3 was developed (obtained from Dr D Wreschner, Tel Aviv University, Israel). Mice received a 0.2 ml subcutaneous injection of appropriate tumour cell dose in PBS and subsequent tumour growth measured. All measurements were performed with dial gauge callipers (Schnelltaster, H C Kroplin, Hessen, Germany) and the size of the tumours were expressed by the area of the tumour size (cm$^2$) (diameter×diameter). The murine DBA/2 mastocytoma cell lines P815, and MUC1$^+$ P815 (containing the cDNA of the membrane anchored form of MUC1) were obtained from Dr B Acres (Transgene, Strasbourg, France).

Rat Mabs to murine CD3 (KT3.2), CD4 (H129.19) and CD8 (53-6.72) were prepared from ascites and tissue culture supernatants (12 to 14). Ascites fluid were prepared in SCID mice as described previously (15). Mice treated with anti-CD3, anti-CD4 and anti-CD8 antibodies were given three intraperitoneal injections of 0.2 mls on days −2, 0 and +2 (0=day of tumour injection). MUC1 antibodies used were VA1 and VA2, produced against a GST-MUC1 bacterial FP which contains five VNIR repeats (16).

Preparation of Peptides and HMFG

Peptides C-p13–32 (C-PAHGVTSAPDTRPAPGSTAP) (MUC1 VNTR) and T4N1 (KTLVLGKEQESAELPCEY) (mouse CD4 N-terminal region peptide) were synthesized using an Applied Biosystems Model 430A automated peptide synthesizer. HMFG was isolated from human milk and prepared as previously described (17).

Enzyme Linked Immunosorbent Assay (ELISA)

(a) Measurement of anti-fusion protein antibody: The ELISA test was performed (17), where 20 g/ml of FP was coated in the wells of a microtitre plate, non-specific binding blocked with 2% bovine serum albumin, and 50 μl of serum from FP and mannan-FP immunized mice added for two hours at room temperature. Normal mouse serum (NMS) was used as negative control. After washing, sheep anti-mouse immunoglobulin conjugated to horseradish peroxidase conjugate (Amersham, United Kingdom) was added, incubated at room temperature and the plate was developed using 50 μl, 0.03% 2,2'-azino-di (3-ethylbenzthiazoline sulphonate (Amersham, United Kingdom), 0.02% $H_2O_2$ (100 Volume, Ajax Chemical) in 0.1M citrate buffer, pH4.0 and incubated for ten to fifteen minutes at room temperature until the desired intensity was achieved. Absorbency was read at 405 nm in a plate reader.

(b) Determination of the activity of fusion protein after conjugation to mannan: The ELISA test was performed as described above with the following modifications; 20 μg/ml of FP, mannan-FP and mannan were coated on the plate and the primary antibodies used were VA1 and VA2 (anti-FP Mabs).

Induction of DTH

To induce DTH in mice, cyclophosphamide (Endoxan-Asta, Mead Johnston) at a dosage of 200 mg/kg body weight, was injected into the peritoneal cavity two days before an intraperitoneal injection of 5 μg mannan-FP. Six days later, the hind footpads were injected (20 μl) with either 10$^5$3T3 or MUC1$^+$3T3 (freeze/thawed five times), 50 μg of HMFG, FP, C-p13–32 (coupled to keyhole-limpet haemocynin using glutaraldehyde), T4N1 (an irrelevant peptide), mannan-FP, GST and mannan and an equivalent volume of PBS. The DTH response was measured at forty eight hours later, by measuring the width and the thickness of the footpad and calculating their product. All measurements of footpads were performed with dial gauge callipers (Schnelltaster, H C Kroplin, Hessen, Germany).

Cytotoxic T-lymphocyte Assay

BALB/c mice immunized with mannan-FP were sacrificed and their spleen cells were collected and washed in 2% foetal calf serum/PBS. The target cells, P815 and MUC1$^+$ P815 cells were either not treated or treated with 5 mM phenyl N-acetyl-a-D-galactosaminide (pagal) for two days (to inhibit O-linked glycosylation) (Sigma, St Louis, USA) prior to use in a standard $^{51}$Cr release assay. Tumour cells (10$^6$ cells) (target cells) were radiolabelled with 100 μCi of Na$_2$$^{51}$CrO4 (Amersham Corp, Arlington Heights) for sixty minutes at 37° C., followed by extensive washing. Spleen cells and target cells, were resuspended in culture medium, and then combined at various effector-to-target ratios in 96-well, U-bottom plates (Costar Corporation). The plates were then centrifuged at 100×g for three minutes to initiate cell contact and incubated for four hours at 37° C. in 10% CO2. After incubation the supernatants were collected and radioactivity was quantitated in a gamma counter (Beckman Instruments).

Spontaneous release of $^{51}$Cr was determined by incubation of the target cells alone, while maximum release of $^{51}$Cr was determined by treatment with 10% sodium-dodecyl sulphate and percentage of specific release was determined as [(experimental−spontaneous)/(maximum−spontaneous)]×100%.

T Proliferation Assay

Mice immunized with M-FP were sacrificed, their spleen cells were collected, washed in 2% foetal calf serum/PBS, red blood cells lysed with 0.14% NH$_4$Cl and duplicate cultures of 5×10$^5$ spleen cells in 100 μl of culture media were seeded in a 96-microwell plate. Spleen cells were stimulated with 100 μl of the following: 10 μg–T4N1, GST, mannan, HMFG, Cp13–32, FP, MFP; and 10$^5$ breast cancer cells (pagal treated and untreated) of −3T3, MUC1$^+$3T3, P815, MUC1$^+$P815, and 10$^5$ human breast cancer cell lines −T47D, MCF7 and ZR15. All tumour cells were treated with 25 μg/ml of mitomycin-C (Sigma, Victoria Australia) for two hours at 37° C. to inhibit proliferation of the tumour cells. Cultures were incubated at 37° C. in 5% $CO_2$ for thirty six hours. $^3$[H]TdR (Amersham, United Kingdom) (6.7 Ci/mmol) incorporation was determined during the last four hours of culture (1 μCi/well).

EXAMPLE 2

Serological Analysis of MUC1$^+$3T3 Cells

In vitro MUC1$^+$3T3 cells did not appear to be different to normal 3T3 cells as they had the same appearance and growth characteristics. By serological analysis, MUC1$^+$3T3 cells expressed high concentrations of MUC1 and were H-2$^{d+}$. Antibodies to MUC1 VNTR peptides reacted with MUC1$^+$3T3 and MUC1$^+$P815 similarly to the human breast cancer cell lines T47D and MCF7 (typing with anti-HMFG: BC2 antibody, anti-fusion protein: VA1 and VA2 antibodies, and anti-MUC1 peptide antibodies: BCP7, BCP8, BCP9 and BCP10). However the murine tumour was differently glycosylated than the human tumour as MUC1$^+$3T3 and MUC1$^+$P815 cells were reactive with anti-carbohydrate (3E1.2) antibody (epitope: glycolylsialyl-Tn) but not with other antibodies to carbohydrate (CC5—epitope: blood group Le$^a$). This shows that the-protein antigens are intact, but the glycosylation is altered. This is not surprising as mice and humans have different glycosyl transferases and therefore different patterns of glycosylation. However, after removal of sugars by pagal treatment, the antibodies to MUC1 VNTR (non-APDTR reacting antibodies) which previously had weak or no reaction with cell lines, became reactive as their epitope has now exposed. There was no difference noted with the (AP)DTR(PA) reactive antibodies.

There was a major difference in reactivity with the carbohydrate reactive antibody (3E1.2) where the staining became weak or negative after pagal treatment, indicating that the pagal was indeed removing O-linked sugars as the epitope of 3E1.2 is O-linked to the protein core of the mucin (18). The typing was repeated at different times and the same results were obtained, which indicated that the phenotype was stable (not shown).

In vivo Growth of MUC1$^+$3T3 Cells

BALB/c mice received a subcutaneous injection of 5×10$^6$ MUC1$^+$3T3 or 3T3 cells and the subsequent growth measured; 3T3 cells grew progressively and were not rejected, as would be expected in BALB/c mice. By contrast the MUC1$^+$3T3 cells grew progressively until day 10 when they started to shrink and had gradually disappeared by day eighteen. Thus, the human MUC1$^+$ gene product appears to confer an immunogenicity on 3T3 cells, leading to their rejection. This was indeed the case as the subsequent challenge with 5×10$^6$ MUC1$^+$3T3 or 3T3 cells demonstrated the total resistance in immunized mice to the growth of MUC1$^+$ 3T3 cells, whereas 3T3 cells grew—that is, the immunogenicity was found only in MUC1$^+$ bearing tumours and was specific for this antigen. Specificity and memory indicate an immune response to MUC1$^+$ and not some other effects such as MUC1$^+$ effecting the growth properties of 3T3. After several weeks of repeated experiments using tumours passaged in vivo, we noted that not all of the mice rejected their tumours and up to 30% of MUC1$^+$ tumours continued to grow. When these tumours were excised and MUC1$^+$ measured serologically, a proportion of cells in the tumours were MUC1$^-$, that is, some of the MUC1$^+$ transfected cells had lost their capacity to express MUC1$^+$ in vivo (we did not determine whether the genes were still present). Such observations have been reported elsewhere with rat tumours (19), presumably due to unstable expression of MUC1. In all our future studies we-ensured that tumours were 100% MUC1$^+$ when used, by serologically testing the MUC1 expression with the anti-HMFG antibody BC2.

T-cell Immune Responses to MUC1$^+$3T3 Cells

Cellular immunity was most likely to be the mode of rejection as it is the commonest mode of rejecting tumour allografts in mice. This was confirmed by the ability of anti-CD3 antibodies to totally abrogate immunity. To determine whether CD4$^+$ or CD8$^+$ cells were responsible for rejection, mice received multiple doses of anti-CD4 or anti-CD8 antibody as these were known to cause immunosuppression in other models (20, 21). Functional CD4 cell depletion by blocking had a transient effect on tumour growth, and tumours were rejected in a similar fashion to untreated mice. By contrast, anti-CD8 treatment led to prolonged tumour growth. We conclude that CD3$^+$ cells are totally responsible for rejection, CD4$^+$ cells have a minimal effect and CD8$^+$ cells are the major effectors of graft rejection. It was noted that in anti-CD8 treated mice, the tumours were smaller than those receiving anti-CD3— clearly the anti-CD8 antibody was not as effective as total T-cell removal with anti-CD3 antibody. CD4 cells having a minor effect was unlikely as the combined action of anti-CD4 and anti-CD8 was no better than anti-CD8 alone. However, we noted that anti-γ-interferon (γIFN) treatment (of no effect used alone) combined with anti-CD8 gave a similar effect with anti-CD3; thus γIFN plays a role in tumour graft rejection, which is mediated by CD8$^+$ cells and γIFN.

Thus, MUC1$^+$3T3 cells could immunize BALB/c mice against MUC1 carried on the 3T3 cells and gave rise to cellular immunity expressed by CD3$^+$8$^+$ cells but not by CD3$^+$4$^+$ cells; there was little humoral immunity as no anti-MUC1 antibodies were found. To measure the various parameters of the immune response, we examined (a) delayed type hypersensitivity and (b) cytotoxic T-lymphocytes.

(a) Delayed type hypersensitivity: Clearly the immune response was cellular and due to CD8$^+$ cells. To determine whether this also involved a DTH response (usually considered to be mediated by CD4$^+$ cells) or a cytotoxic T-cell response (usually CD8$^+$), mice were immunized with MUC1$^+$3T3 cells and a DTH was performed by injecting the hind footpads with various antigens. Preliminary studies demonstrated that in the absence of cyclophosphamide no measurable DTH responses occurred. A DTH response was detected in the footpads injected with killed (freeze/thawed 5 times) MUC1$^+$3T3 cells and a weaker response when challenged with either HMFG, fusion protein-GST and Cp13-32-KLH. These responses were clearly specific as 3T3 cells elicited no response. To determine whether the DTH response was mediated by CD4$^+$ or CD8$^+$ cells, mice were injected with anti-CD4 and anti-CD8 antibodies and the DTH response measured. Anti-CD4 totally blocked DTH reactions, anti-CD8 partially blocked DTH reactions, but to a lesser extent, when challenged with MUC1+3T3 cells, Cp13-32, HMFG and fusion protein. Thus the cells which cause the effective immune response to human MUC1 (CD8) were not the same as those eliciting a DTH response, although CD8$^+$ cells certainly contributed to the DTH.

b) Cytotoxic T-lymphocytes: Cytotoxic assays were performed and after MUC1$^+$3T3 cell immunization there was up to 60% lysis of MUC1$^+$P815 targets treated with pagal. Untreated MUC1$^+$P815 targets and non-transfected P815 targets were not lysed. Pagal treated and non-treated 3T3 and MUC1$^+$3T3 targets also gave no lysis—possibly as 3T3 cells are poor targets for Tc assays. To determine the phenotype of the Tc, anti-CD4 and anti-CD8 antibodies were used in blocking studies—the anti-CD8 reagent (53-6.7) was known to be capable of blocking T-cell lysis by CD8$^+$ cells. This proved to be the case in these studies as anti-CD8 could block Tc, whereas anti-CD4 and a control antibody had little effect. Since only Tc were found to pagal treated MUC1$^+$P815 targets, and since non-APDTR reactive anti-MUC1 antibodies (VA1, BCP7, BCP9 and BCP10) became reactive with pagal treated MUC1$^+$3T3, MUC1$^+$P815, T47D and MCF7 cells, it is clear that both the antibody reactive and T-cell reactive epitopes are hidden, and both exposed after pagal treatment.

Mice resistant to MUC1$^+$3T3 cells have CD8$^+$ T-cell immunity, CD4$^+$ DTH, a detectable Tc response due to CD8$^+$ cells, and no antibody (see below). As the Tc response (at least at the level of the T-cell phenotype) correlated with the effector cell phenotype in rejecting tumours, it would appear to be the more appropriate response to measure.

Immune Responses—B Cells

While it was shown above that cellular immunity was effective and little antibody was made, the role of antibody was not clear. Further, mice generally make poor antibodies and mobilize complement so poorly that they are not the species of choice on which to study antibody mediated destruction of grafts, unless certain conditions are met—a) the provision of sufficient antibody (be it polyclonal or monoclonal); b) the provision of sufficient complement; c) high density of surface antigens. The MUC1$^+$ antigen density is high so additional antibody and complement were provided. In addition, the mice were immunosuppressed with CD3 to remove any component of cellular immunity (22). In spite of large amounts of antibody and complement (as described in materials and methods) (capable of rejecting skin allograft and xenografts), the tumours grew progressively—indeed, at the same rate as in mice not receiving antibody. Thus, antibody and complement are unable to cause rejection of MUC1$^+$3T3 cells.

Immunization with HMFG, Peptides and Fusion Protein

The preceding defines a model of the murine immune response to human MUC1 transfected into 3T3 cells and forms the basis for using various immunogens to generate a similar or greater immune response with synthetic materials as that produced with cellular MUC1. The aim was clearly to substantially decrease tumour growth after immunization. As immunogens, natural mucin (HMFG), synthetic products—MUC1 peptides made of VNTR dimers, and a 5×VNTR repeat fusion protein were used. It should be noted that without prior immunization, tumours are rejected after eighteen days—such mice then being resistant to a subsequent challenge. Thus there is a "window" of approximately eighteen days when tumours will be rejected. So that, immunization could lead either to no tumours appearing or to reduced size during this time.

To examine the immunogenicity of HMFG, fusion protein and synthetic peptides groups of 15 BALB/c mice were immunized with 50 μg of these materials and challenged with 1–5×10$^6$ 3T3 or MUC1$^+$3T3 cells. The 3T3 cells had the same progressive growth in all immunized and non-immunized mice, so there were no non-specific effects of the immunization procedures. When mice were challenged with the lower dose of 1×10$^6$ cells, significant differences were noted as compared to the non-immunized control. Thus, on day six, mice immunized with either the peptide or fusion protein had tumours approximately 25% that of controls; immunizing with HMFG was less effective, tumours being approximately 60% the size of controls. However when challenged with 5×10$^6$ MUC1$^+$3T3 cells, there was some difference in tumour size, compared to the controls, but not as obvious by challenging with a lower dose. As expected with subsequent tumour challenge, the peptide immunized mice which had rejected the tumour were now resistant to tumour challenge. Thus, immunizing mice with peptides, fusion proteins or HMFG and challenging with a low dose of MUC1$^+$3T3 cells gave rise to some anti-tumour effect. Although the VNTR containing peptide, fusion protein and HMFG gave some degree of protection, mice immunized with the N- and C-terminal peptides of MUC1 had no significant protection indicating that these peptides do not induce immunity to MUC1, and also showing that the immunization procedure itself was without effect. To measure the various parameters of the immune response, we examined (a) MUC1 antibody production, (b) delayed type hypersensitivity and (c) cytotoxic T-lymphocytes.

(a) Antibody: Immunized mice with peptides, fusion protein or HMFG had high levels of anti-MUC1 antibody both before and after tumour injection. Thus, immunization gave rise to high levels of antibody, but apparently little cellular immunity as shown by a minor effect on the tumours. It was of interest that mice immunized with the control peptide (T4N1), and which had rejected the tumour did not produce antibodies against MUC1; nor did the mice immunized with peptide and other immunogens have an increase in antibody titre after rejecting the tumour.

(b) DTH: Mice immunized with HMFG, Cp13-32 and fusion protein-GST had DTH responses to the various MUC1 antigens and which could be inhibited by CD4 (totally) and CD8 (partially) antibodies. Thus, immunization with the three agents gave rise to some degree of cellular immunity but not sufficient to greatly inhibit tumour growth.

(c) Cytotoxic T-lymphocyte assay: Tc assays were performed from spleen and lymph node cells of immunized mice and no cytotoxic cells were detected. Thus the various immunization procedures appeared to bias the immune response to antibody production, rather than cellular immunity.

Table 2 summarizes the differences in immunizing with cellular and synthetic antigens.

TABLE 2

Differences in immunizing with cellular and synthetic antigens

| Immunogens | Tumour rejection | Antibody | DTH | Tc |
|---|---|---|---|---|
| Tumour | +++ | + | +++ | + |
| MUC1 $^+$3T3 | | | | + |
| | | | | + |
| Peptide | + | +++ | +++ | − |
| Fusion protein | + | +++ | +++ | − |
| HMFG (mucin) | + | +++ | +++ | − |

+++ = high; + = low; − = absent

EXAMPLE 3

Analysis of M-FP

The MUC1 FP was bound to mannan using periodate as described in the materials and methods. The amino groups of the FP reacts with aldehyde residues of the oxidized mannan to form the labile Schiff base (Scheme 1). Free mannan and FP was not separated from conjugated mannan. Elution profiles for $^{125}$I-FP and $^{125}$I-M-FP obtained by gel filtration chromatography demonstrated that the mannan-fusion protein eluted as two peaks (201 Kd and 73 Kd). The FP eluted as two peaks: 38 Kd and 20 Kd (this lower peak may be GST due to cleavage of FP). Autoradiography analysis of $^{125}$I-FP and $^{125}$I-M-FP showed that most of the FP has been conjugated to mannan.

The activity of FP after conjugation to mannan determined by an ELISA test showed that the FP had retained all its activity.

In vivo Growth of MUC1$^+$3T3 Cells

BALB/c mice which received a subcutaneous injection of 5×10$^6$ MUC1$^+$3T3 cells grew progressively until day ten when they started to shrink and disappeared by day eighteen, whereas 3T3 cells were not rejected as expected by BALB/c mice as set out in Example 2 (FIG. 1). Thus, the human MUC1$^+$ gene product confers an immunogenicity on 3T3 cells, leading to their rejection, and such mice were totally resistant to subsequent challenge. Cellular immunity was the mode of rejection as anti-CD3 and anti-CD-8 antibodies totally abrogated immunity.

Immunization with Mannan-Fusion Protein

Figure 2B:
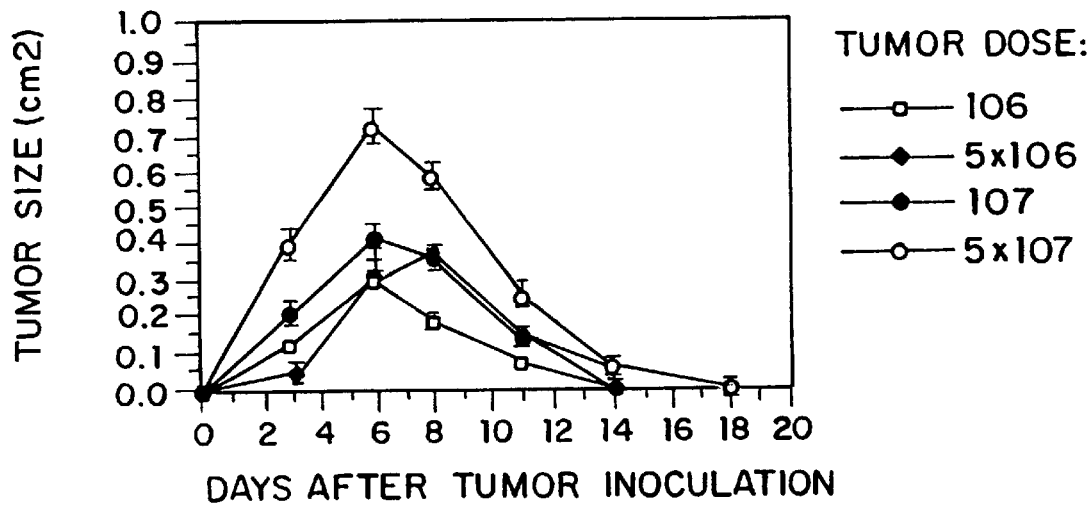
Figure 3A:
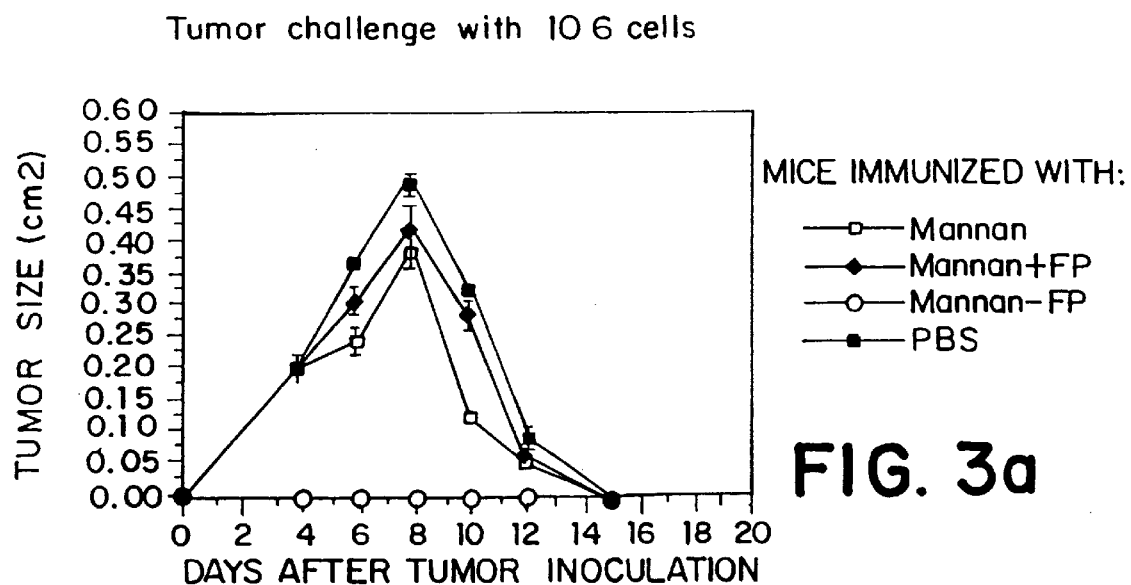
Figure 3B:
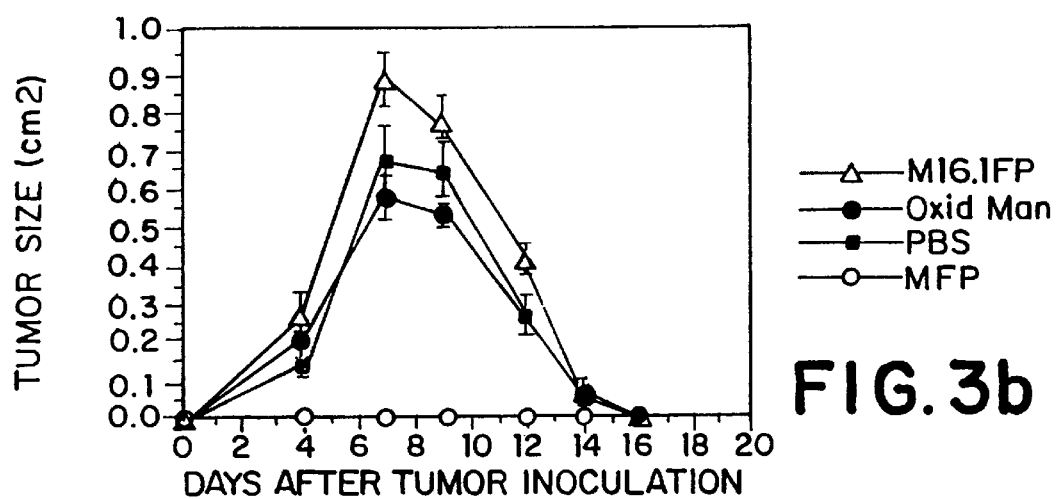
Figure 3C:
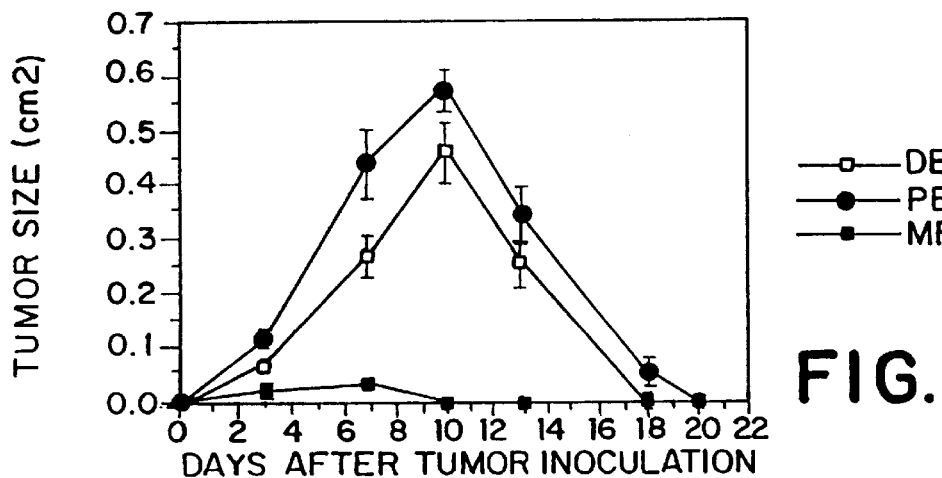

To examine the immunogenicity of the mannan-FP, groups of ten BALB/c mice were immunized with 5 μg mannan-FP (5 μg corresponding to the amount of FP) and challenged with 10$^6$–5×10$^7$ MUC1$^+$3T3 cells. There was no obvious tumour growth in immunized mice (FIG. 2A) as compared to non immunized mice (FIG. 2B). To show that the mannan-FP conjugate gave rise to specific anti-tumour immunity and that mannan or FP alone were without effect, mice were immunized with an equivalent dose of mannan (as in the conjugate=7 mg/ml), a mixture of mannan and FP and a group of non immunized mice and were challenged with 10$^6$ MUC1$^+$3T3 cells. Mice immunized with mannan-FP conjugate, no tumour growth was observed whereas mice immunized with mannan alone and a mixture of mannan and FP, tumours grew no different as compared to non immunized mice (FIGS. 3A, 3B and 3C). Thus, protection of tumour growth was specific for the conjugate and mannan and FP alone was without effect. Mannan-FP immunized mice were challenged with $10^6$ 3T3 cells and the 3T3 cells had the same progressive growth in immunized and non-immunized mice (FIG. 4), indicating that there were no non-specific effects of the immunization procedures.

Immune Response to M-FP

Anti-CD3 antibody could totally abrogate immunity in mice immunized with M-FP (FIG. 5) and mice which received anti-CD4 or anti-CD8 antibodies showed the following effect: CD4 immunosuppression had a minor effect on tumour growth (FIG. 5); by contrast anti-CD8 treatment led to prolonged tumour growth. Thus $CD3^+/CD8^+$ cells are totally responsible for the immunity and tumour protection, $CD4^+$ cells had a minimal effect (FIG. 5). Thus M-FP could immunize against MUC1 carried on the 3T3 cells giving rise to cellular immunity expressed by $CD3^+/CD8^+$ cells but not by $CD3^+/CD4^+$ cells. To measure the various parameters of the immune response, we examined (a) delayed type hypersensitivity, (b) cytotoxic T-lymphocytes (c) Tell-cell proliferation and (d) antibody production.

(a) Delayed type hypersensitivity: DTH responses (usually considered to be mediated by $CD4^+$ cells) were performed by injecting the hind footpads with the various antigens (FIG. 6). A DTH response was detected in the footpads challenged with killed (freeze/thawed five times) $MUC1^+$ 3T3 cells, HMFG, FP-GST, Cp13-32-KLH, mannan-FP and a weaker response to GST (as GST is part of the FP) (FIG. 6). These responses were clearly specific as killed 3T3 cells, mannan alone, an irrelevant peptide (T4N1) and PBS could elicit no responses. To determine whether the DTH response was mediated by $CD4^+$ or $CD8^+$ cells, mice were injected with anti-CD4 and anti-CD8 antibodies and the DTH response measured. Anti-CD4 totally inhibited DTH reactions, anti-CD8 inhibited but to a lesser extent (FIG. 6). Thus the cells which caused the effective immune response to human MUC1 ($CD8^+$ cells as shown in FIG. 5) were not the same as those eliciting a DTH response, although $CD8^+$ cells certainly contributed to the DTH.

(b) Cytotoxic T-lymphocytes: Cytotoxic assays were performed and it was shown that after M-FP immunization there was 30% MUC1 specific lysis of $MUC1^+P815$ targets treated with pagal (FIG. 7). Untreated $MUC1^+$ P815 targets gave 15% MUC1 specific lysis whereas non-transfected P815 targets were not lysed (FIG. 7). It is likely that these cells were $CD8^+$ (12).

(c) T cell proliferation: Proliferation assays were performed and it was shown that after M-FP immunization there were proliferative T-cells to M-FP, FP, Cp13-32, HMFG, and to pagal treated and untreated $MUC1^+$3T3, $MUC1^+$ P815 cells. Other stimulants had no effect.

(d) Antibodies to Mannan GST-MUC1 fusion protein conjugate: Mice were bled and their sera tested by ELISA for anti-FP antibodies. No anti-FP antibodies were detected compared to mice immunized with FP alone. Plates coated with mannan coupled to BSA were used to detect anti-mannan antibodies and no anti-mannan antibodies were detected. Normal mouse serum was as a negative control.

Thus, mice made totally resistant to $MUC1^+$3T3 cells by immunizing with FP coupled to mannan have $CD8^+$ T-cell immunity, $CD4^+/CD8^\pm$ DTH, a detectable Tc response due to $CD8^+$ cells, proliferative T-cells to the specific to the immunizing antigen, and little humoral immunity as no anti-MUC1 antibodies were found M-FP appears to be able to induce an anti-tumour response, similar to that shown with tumour cell rejection (12).

M-FP in Therapy

Figure 8A:
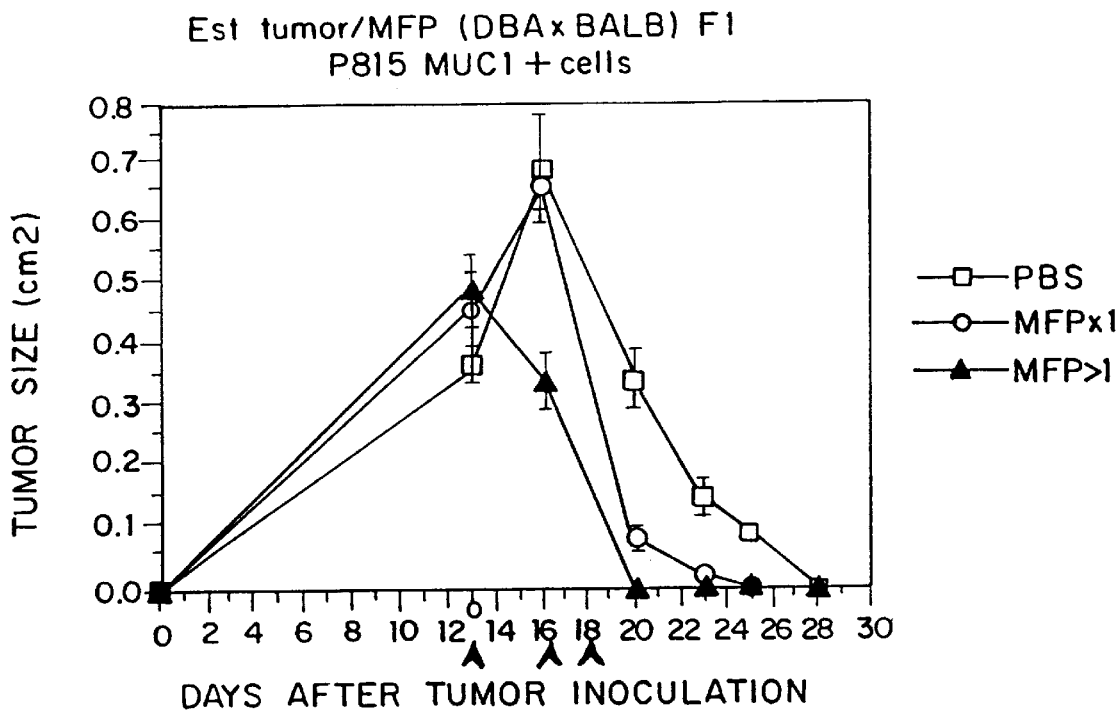
Figure 8B:
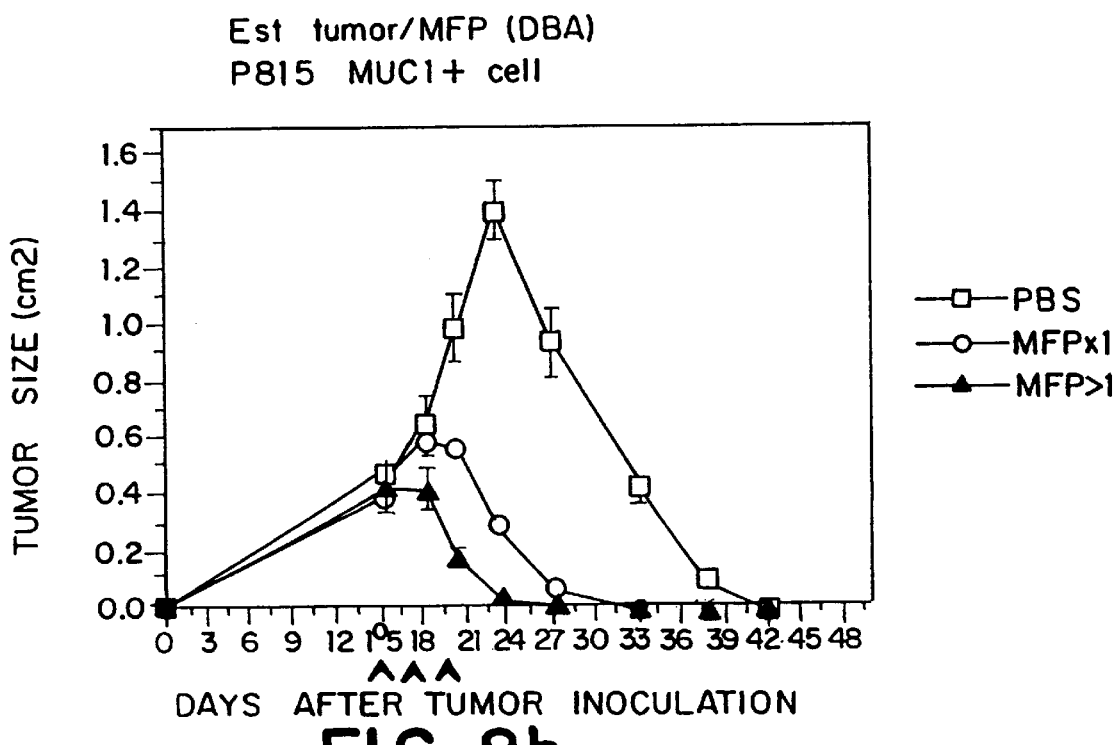

To determine the effectiveness of M-FP as a therapeutic agent against established tumours, injections of MFP were delayed until tumours were established. $MUC1^+P815$ cells grow progressively in (DBA/2×BALB/c)F1 mice, when given subcutaneously, until day sixteen to twenty when they start to shrink and usually disappear by day twenty-eight (FIG. 8A). To examine the effectiveness of M-FP on established tumours, groups of five (DBA/2×BALB/c)F1 mice were injected with $5\times10^6$ $MUC1^+P815$ cells; thirteen days later, the mice were injected with 5 μg M-FP (5 μg corresponding to the amount of FP) once, or every other day. Tumours in control mice (injected with PBS) were rejected by day twenty-eight. However, mice injected regularly began to reject their tumours immediately, the tumours rapidly disappearing by day twenty. A single injection also gave rise to more rapid rejection (FIG. 8A).

Another model was examined using $MUC1^+P815$ cells in DBA/2 mice, which grow until day twenty-two to thirty when they shrink and usually disappear by day forty two. $MUC1^+P815$ cells were injected subcutaneously and on day fifteen DBA/2 mice were injected with MFP. In the control group mice injected with PBS, tumours were rejected by day forty-two whereas mice immunized with MFP once on day fifteen tumours were rejected by day thirty-three (FIG. 8B) compared with mice immunized every other day, tumours were rejected by day twenty-seven with a rapid reversal in their growth after a single injection. Thus, not only do pre-immunized mice have an anti-tumour effect, his can be obtained with established tumours.

EXAMPLE 4

A patient suffering from breast cancer was injected with 50 μg of the mannan fusion protein produced according to Example 1. No side-effects were seen following immunization. The therapeutic treatment of the patient's cancer is currently under evaluation and it has already been observed that several lesions in the bone have disappeared.

EXAMPLE 5

The VNTR's of mucins MUC1 through MUC6 are coupled to mannan and other carbohydrates according to standard procedures such as described in Example 1. Table 3 sets out a description of the various mucin core proteins.

TABLE 3

Description of human mucin core proteins, cDNA's and genes

|  | MUC1 | MUC2 | MUC3 | MUC4 | MUC5 | MUC6 |
| --- | --- | --- | --- | --- | --- | --- |
| Tissue | Breast, ovary, pancreas [a]GI, [b]GU and [c]resp. tract | GI and resp. | GI tract | Resp. tract | Trachea Bronchus ± Stomach | Stomach gall bladder |
| Polymorphism | Yes | Yes | Yes | ? | ? | ? |
| Chromosome | 1q21 | 11p5.5 | 7q | 3 | 11p15 | 11015.4/5 |
| Molecular weight of protein kDa | 120–240 | 160 | 190–320 | ? | ? | ? |
| Base pairs | 60 | 60 | 51 | 48 | 24 | 507 |
| VNTR*([d]aa/repeat | 20 | 23 | 17 | 16 | 8 | 169 |

[a]Gastrointestinal;
[b]GU - Gastrourinary;
[c]Resp. - Respiratory;
[d]aa - amino acids
*MUC1 VNTR - SAPDTRPAPGSTAPPAHVT
MUC2 VNTR - PTTTPISTTTMVTPTPTPTGTQT
MUC3 VNTR - HSTPSFTSSITTTETTS
MUC4 VNTR - TSSASTGHATPLPVTD
MUC5 VNTR - PTTSTTSA (494 base pair insert - eight amino acid tandem repeat)
MUC6 VNTR - 169aa repeat unit
MUC7 VNTR - TTAAPPTPPATTPAPPSSSAPPE

EXAMPLE 6
MHC Restriction of CTL's after MFP Immunization

To determine whether the CTL's produced in mice were MHC or indeed, Class I MHC restricted, mice were immunized with MFP (5 μg weekly×3) and their spleen cells removed and used as CTL's against various $^{51}$Cr labelled target cells. The results demonstrate that:
a) Immunizing H-$2^d$ mice (DBA/2, NZB, BALB/c or B10.D2) gave CTL's against P815-Tm211 (MUC1$^+$) P815 cells but not against P815-MUC1 cells.
b) When mice of other H-2 haplotypes were immunized, no CTL's were found on testing the H-$2^d$ P815 MUC1$^+$ cells (in particular H-$2^b$; C57BL/6; 129 and BALB.B; H-$2^k$: CBA; H-$2^s$: SJL and H-$2^w$: NZW. Of interest in these studies is the finding that:
BALB/c (H-$2^d$) was +) these are a congenic pair differing only in H-2
BALB.B (H-$2^b$) was −)
B10.D2 (H-$2^d$) was +) these are a congenic pair differing only in H-2
C57BL/6 (H-$2^b$) was −)
This maps the reactivity to the H-2 MHC complex.
c) In other studies it was shown that mice of the H-$2^b$ haplotype had activity for H-$2^b$ (E3 MUC1$^+$ tumour cells), but not for other H-2 haplotypes.

Thus, CTL responses in mice to MFP are H-2 (MHC) restricted.

EXAMPLE 7
T-cell Proliferation to MFP in Mice

Mice were immunized with various MFP (5 μg/week×3) and tested on a range of peptides at different doses in a proliferation assay. In this assay, different peptides are added in different amounts to splenic cells in tissue culture and after forty-eight hours $^3$H-thymidine is added for twenty-four hours. The cells are harvested and the incorporated radioactivity measured. The studies show that:
i) MFP stimulates the proliferation of T-cells from immunized mice in the presence of peptides.
ii) There is a dose response so that peptides
C-p13-32, C-p1-24: 5 mcM is the optimal dose
p13-32, p1-24: 10 mcM is the optimal dose
Ap1-15<1.0 mcM is the optimal dose
p5-20<1.0 mcM is the optimal dose
The sequence numbering is such that:

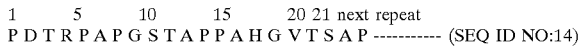

1     5       10       15       20 21 next repeat
P D T R P A P G S T A P P A H G V T S A P ---------- (SEQ ID NO:14)

iii) Of the peptides used:
p5-20 is +
p14-24) are −
p16-24)
The epitope is not likely to be the antibody epitope APDTR, but is in p14-24~possibly GSTAP.

EXAMPLE 8
Phase I Study of Synthetic MUC1 Peptides in Cancer

The aim of this example is firstly to determine whether synthetic or other MUC1 agents are immunogenic in humans and secondly, to determine whether an immune response against a self-peptide has any deleterious effects by reaction on normal tissues containing MUC1—the basis of a Phase I study. Anti-tumour effects are then to be examined.
Materials and Methods
Patients To be eligible to enter the trial, patients had to have histologically proven breast cancer and only those with metastatic disease were considered, particularly those not having received cytotoxic chemotherapy in the preceding-four weeks. The patient had to have given written informed consent and those who were lactating or pregnant were ineligible for the study. All patients had their clinical status documented and base-line blood samples taken for MSA and CASA analyses. The studies undertaken were routine for a Phase I study including history and examination, full blood examination, toxicity notation, collection of blood for creatinine and amylase. Specific testing for immune response to the injected material was done in several ways:
Serological and Cellular Studies
a) the MSA and CASA tests were performed—these detect circulating MUC1 and conceivably alter with an immune response to the antigen (MSA detects a unique carbohydrate antigen; CASA the APDTR peptide).

b) samples were tested for anti-MUC1 antibodies using an ELISA test and testing and separately on diphtheria toxoid, fusion protein, GST, p13-32 synthetic peptide, HMFG and on another peptide (STPA—derived from the sequence of CD46—used as a non-specific negative control).

c) T-cell responses were determined in three ways:
   i) delayed type hypersensitivity reactions—(DTH) performed using standard antigens to determine the patients response to diphtheria or tetanus; response to the injected material (DT-peptide); and separately testing peptide linked to another carrier eg. human serum albumin.
   ii) T-cell proliferation—performed by taking blood from the patient, separating the peripheral blood lymphocytes (PBL) and establishing these in tissue culture with appropriate antigens (see below) and after forty-eight to seventy-two hours adding tritiated thymidine or twenty-four hours and measuring proliferation.
   iii) T-cell cytotoxicity—patients proliferal blood cells were isolated and set up in short term (four hour culture) with $^{51}$Cr labelled target cells consisting of murine cells (MUC1$^+$3T3 and P815) and human tumour cells which express human MUC1 (T47D, BT20).

Finally, the responses of the tumours were monitored in the patients.

Synthesis and Conjugation of Peptides

Peptide C-p13-32 (CPAHGVTSAPDTRPAPGSTAP) derived from the sequence of MUC1 variable number of tandem repeats (VNTR) were synthesized using an ABI peptide synthesizer (Foster City, Calif., United States of America). Peptide STP-A representing the serine, thrionine and proline rich region of human CD46 was used as a negative control. The peptide C-p13-32 was conjugated to diphtheria toxoid (DT) (Special sample, CSL, Melbourne, Australia) using glutaraldehyde. Ten milligrams of peptide C-p 13-32 was reacted with 1250Lf DT in the presence of 5 ml, 0.25% glutaraldehyde at room temperature for six hours, dialysed against phosphate—buffered saline. The conjugate DT-C-p13-32 was filtered (0.22 mm, Millipore) in a laminar flow hood. The activity of DT-C-p13-32 was tested by an anti-MUC1 antibody BC2. The sterility and pyrogen tests were performed at the Pharmacology Department, Melbourne University, and Microbiology Department, Austin Hospital, Australia).

Enzyme-linked Immunosorbent Assay (ELISA)

To test human antibody to C-p13-32, various antigens including FP, DT and HMFG were coated onto PVC plates (Costar) in 0.05M carbonate buffer, pH9.6 for two hours at 37° C., and non-specific binding sites were blocked with 2% BSA for one hour at 37° C. After washing with PBS-0.05% between twenty, serum samples at series dilution were added to each well, and incubated at 4° C. overnight. After thorough washing of the plates, sheep anti-human immunoglobulin labelled with horseradish peroxidase (Silenus, Melbourne, Australia) was added to plates and incubated for two hours at ambient temperature. The plates were washed and at the bound human antibodies were detected by the addition of 0.03% 2,2-azinodi (3-ethylbenzthiazoline sulfate) in 0.1M citrate buffer, pH4, containing 0.02% H2O2. The absorbency was measured at 405 nm using an ELISA reader (Bioteck, EL312e). The antigen used in this assay were a) human milk fat globule (HMFG); b) fusion protein, containing five VNTR repeats of MUC1 and glutathione-s-transferase, produced using P-GEX vector; c) DT, d(C-p13-32, and e) negative control peptide STP-A.

To measure circulating MUC1 antigen in serum two commercial kits (MSA assay and CASA assay) (Medical Innovations Limited, Artarmon, NSW, Australia) were used. The MSA assay is an inhibition assay using an anti-MUC1 antibody, the binding of which to the MUC1 can be inhibited by the circulated MUC1 in the sera of patients. The CASA assay is a sandwich ELISA, which used two anti-MUC1 antibodies.

Results

Toxicity: In general, there was little systemic toxicity—particularly with the first injections. Later, local reactions occurred in patients which we presumed to be due to a local DTH reaction to diphtheria toxoid as there was erythema and induration which lasted up to seventy-two hours. In some patients, this was accompanied by enlargement of local lymph nodes. Apart from these reactions after the injection, no other side effects were noted.

Figure 9A:
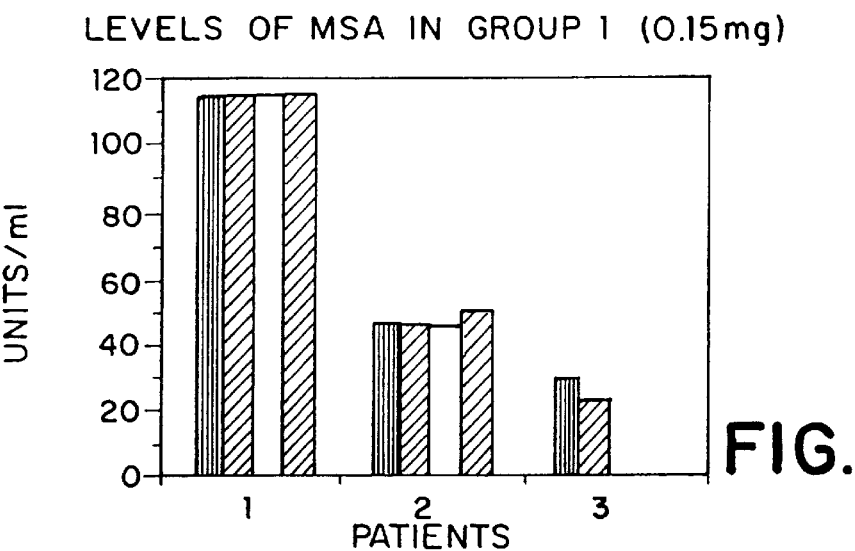
Figure 9B:
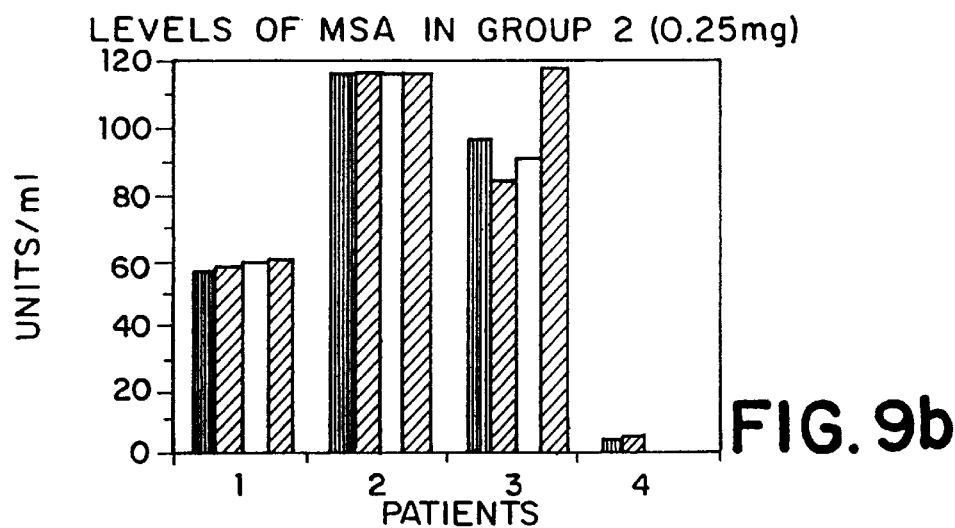
Figure 9C:
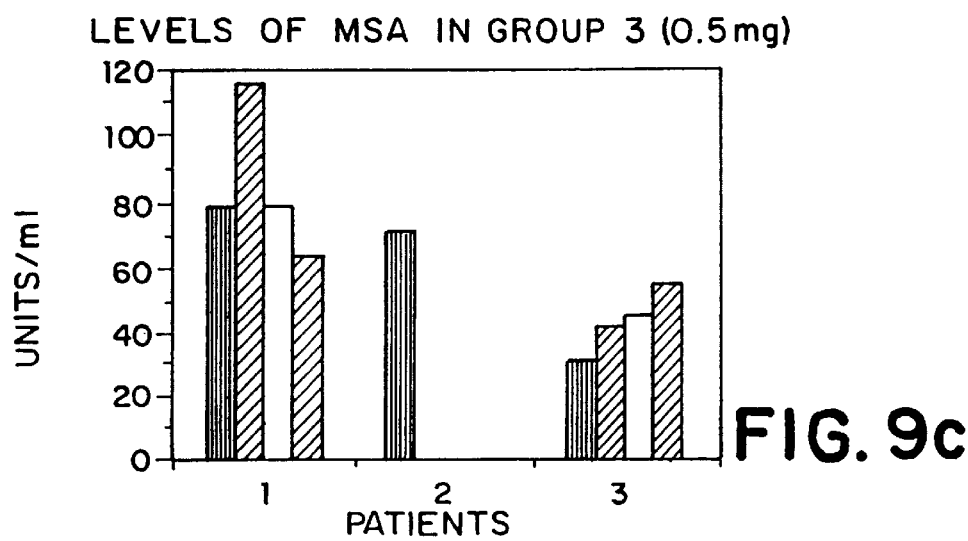
Figure 10A:
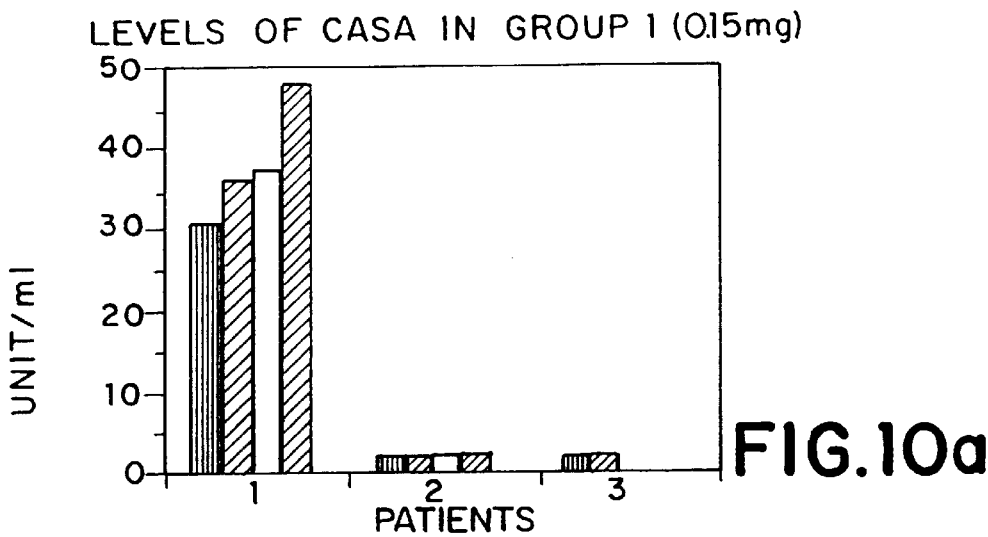
Figure 10B:
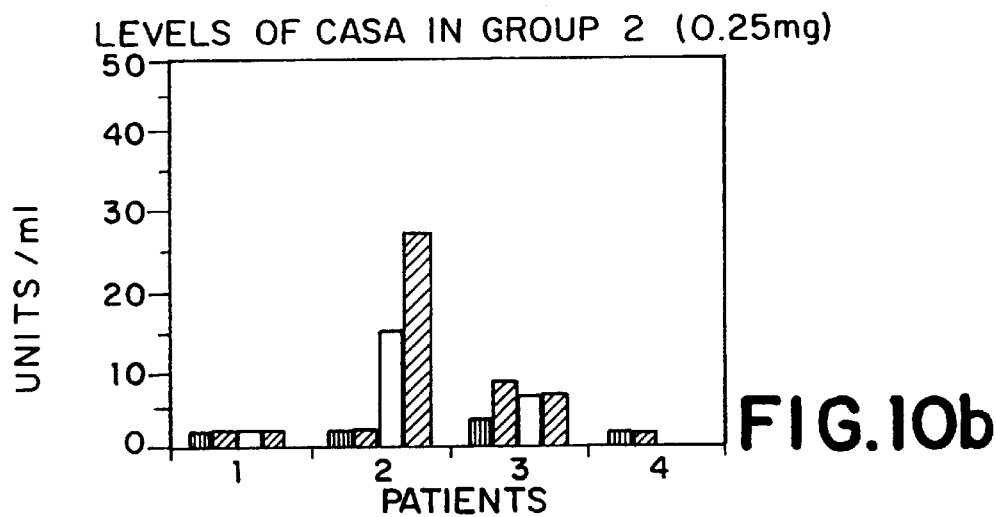
Figure 10C:
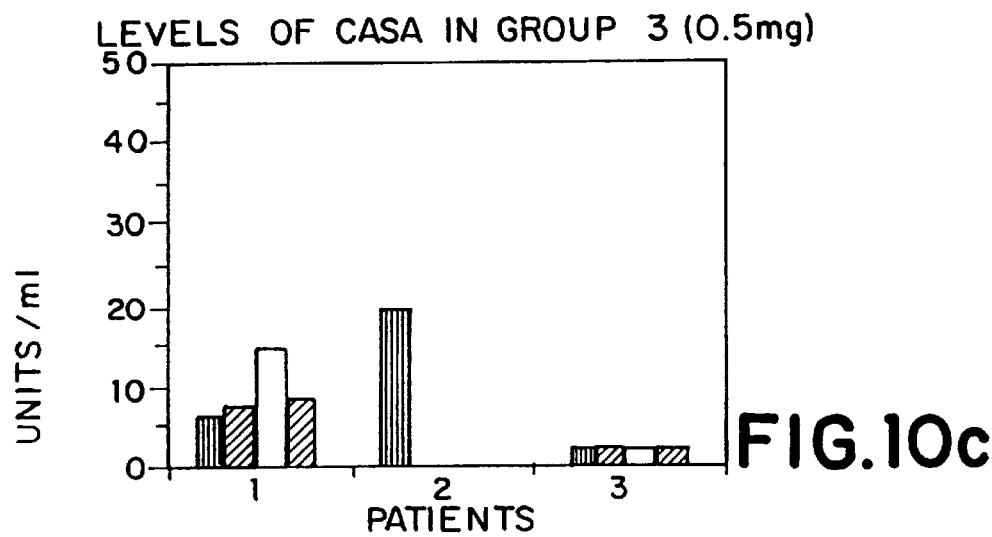
Figure 11A:
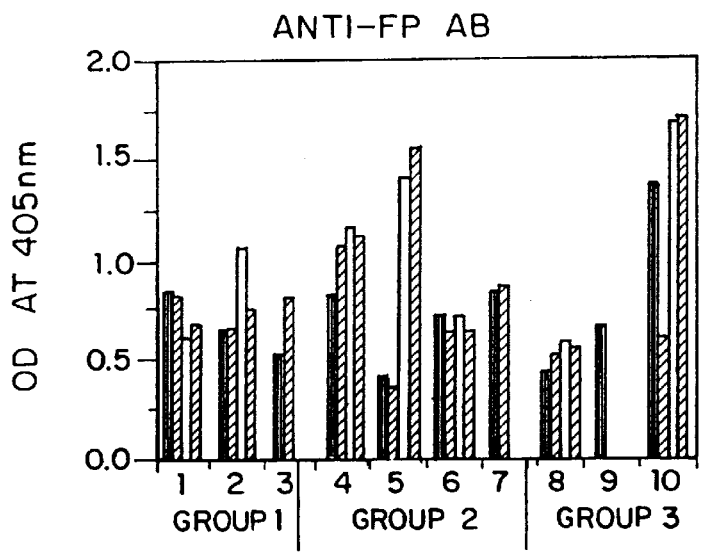
Figure 11B:
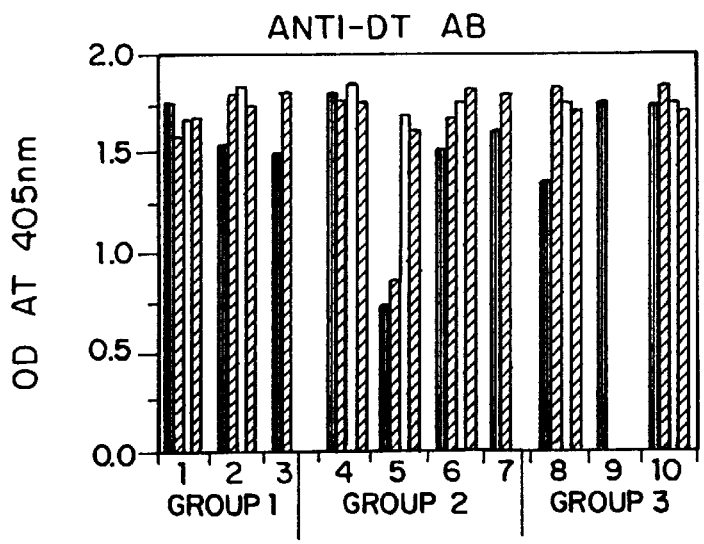
Figure 11C:
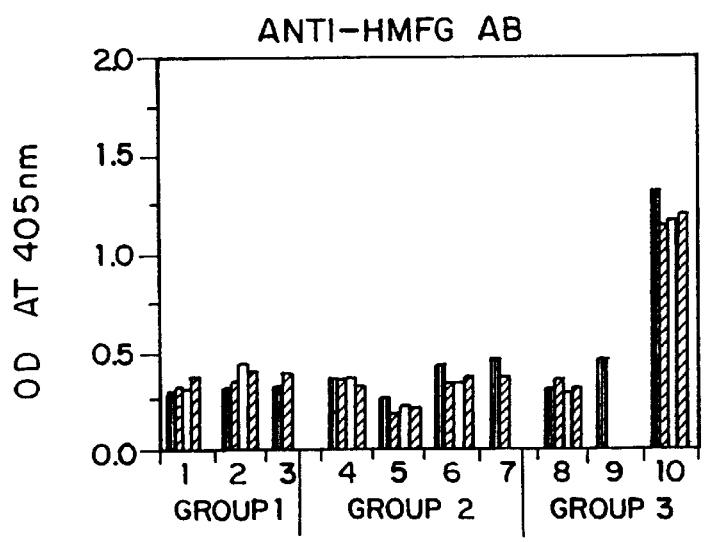
Figure 11D:
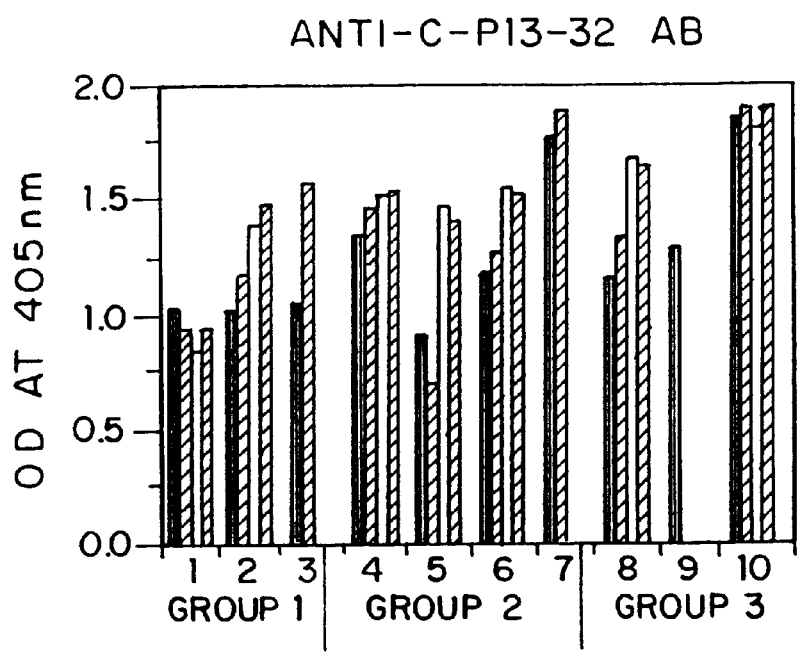
Figure 11E:
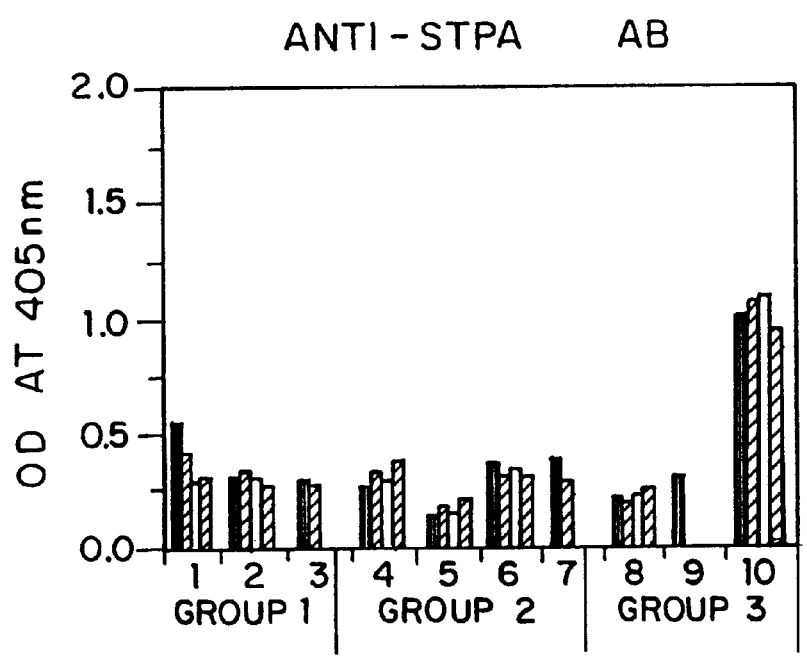

MSA and CASA testing: These tests were performed on most patients and no trends were noted. The data is presented on samples taken at different times during the course of injection and in most patients, there was virtually no increase in the MSA level over the course of the injection (FIGS. 9A, 9B and 9C). Similar comments can be made with the CASA tests (FIGS. 10A, 10B and 10C). In most patients, there was little change in the levels, although in two patients a progressive increase was noted and this correlated with the progressive disease in those patients. It would be appropriate to state there were essentially no changes in the circulating levels of MUC1 detected by these two separate tests over the course of injection and some weeks thereafter.

Anti-MUC1 antibody (FIG. 11): Firstly, we would indicate some difficulty in using human serum samples on synthetic peptides—in most cases there is significant background on the synthetic MUC1 peptides not seen with HMFG or with the STPA non-specific peptide. Thus, the fusion protein and C-p13-32 are non-specifically "sticky". With the exception of several patients, there appeared to be little increase in antibody formation over the course of the injection and we conclude that immunization with peptide gave rise to no antibodies in 10/12 patients. However, in two patients (number 5 and number 10) significant increases in antibodies reacting with fusion protein and anti-C-p13-32 antibodies were noted—and these were specific increases as there was no alteration in the effect on either HMFG or the STPA. In patient number 5, an increase in the diphtheria antibody titre had also occurred, but not in patient number 10. Thus, antibody responses were noted, but not uniformly so.

Skin Testing: Skin testing of patients is still in progress. At the lower doses of 0.15 mg and 0.25 mg was not done and is currently in progress with 0.5 mg and 1 mg doses. At this stage there are no responses to the synthetic peptide, although responses were noted to diphtheria. As indicated, these studies are in progress.

T-cell proliferation: The validity of these assays was shown by the proliferative response found in six of ten normal subjects when tested with diphtheria toxoid—these responses indicating the previous immunization with the toxoid. Also of note was that none of the ten normal subjects had any proliferative responses to the different antigens used, in particular those containing MUC1 (fusion protein, synthetic peptide, C-p13-32, HMFG) or to the murine cell line expressing MUC1 (Mor5). In addition, five of nine separate tests on the patients with cancer showed proliferative responses to DT, although these tests were only performed on six patients. It was of interest that after several courses of injections, four of the six patients showed proliferative responses to MUC1 in one form or another—this was particularly noted on the murine cell line expressing MUC1 on the cell surface, but in two patients, one to C-p13-32 DT and this patient also responded to the fusion protein. None of the patients responded to MUC1 in HMFG nor to the non-specific peptide T4N1. Thus, some proliferative responses were noted in some patients, but not in all.

Tumour Response: In the seven patients with progressive disease, in three the disease was stable.

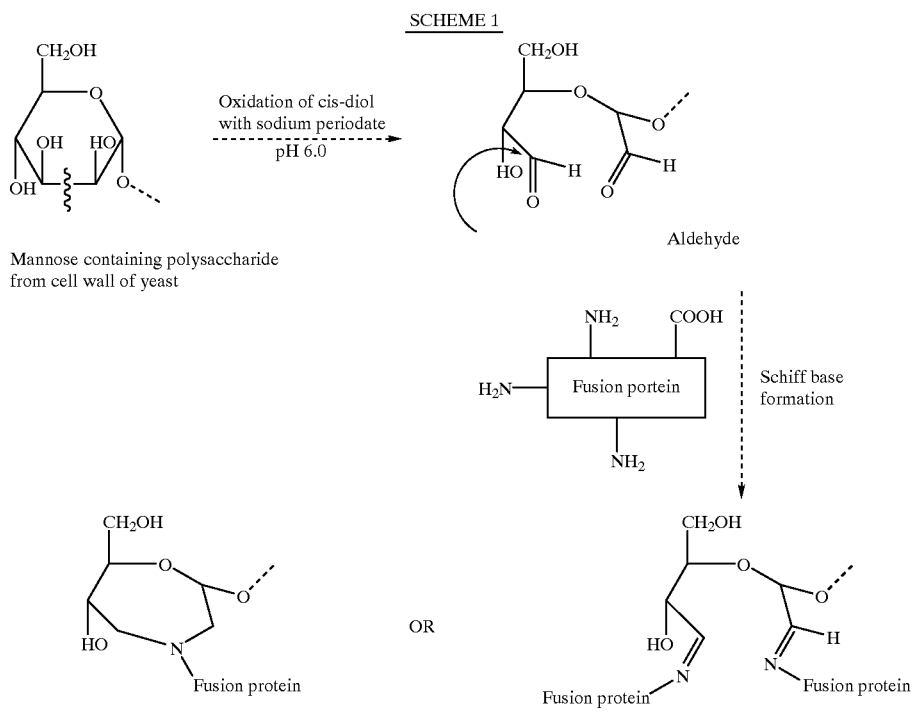

References

1. Gendler, S., Papadimitriou, J. T., Duhig, T., Rothbard, J. & Burchell, J., A highly immunogenic region of a human polymorphic epithelial mucin expressed by carcinomas is made up of tandem repeats., *J. Biol. Chem.*, 263:12820–12823, 1988.
2. Harisch, F. G. & Uhlenbruck, G., Structures of Neutral O-Linked polylactosaminoglycans on human skim milk mucins, *J. Biol. Chem.*, 264: 872–883, 1989.
3. Marjolijn, J. L., Ligtenberg, M. J. L., Vos, H. L., Annemiek, M. C., Gennissen, A. M. C. & Hilkens, J. Episialin, A carcinoma-associated mucin is generated by a polymorphic gene encoding splice variants with alternating amino termini, *J. Biol. Chem.*, 265:5573–5578, 1990.
4. Crocker, G. & Price, M. R., Genetic polymorphism of high molecular weight glycoproteins: A comparative study in normal individuals and breast cancer patients, *Br. J. Cancer*, 55:651–652, 1987.
5. Barnd, D. L., Lan, M. S., Metzgar, R. S., Finn, O. J., Specific, major histocompatibility complex-unrestricted recognition of tumour-associated mucins by human cytotoxic T-cells, *Proc. Natl. Acad. Sci.*, 86:7159–7163, 1989.
6. Jerome, K. R., Barnd, D. L., Boyer, C. M., Taylor-Papadimitriou, J., McKenzie, I. F. C., Bast, R, C., and Finn, O. J., Adenocarcinoma reactive cytotoxic T-lymphocytes recognize an epitope present on the protein core of epithelial mucin molecules. Cellular immunity and immunotherapy of cancer, 321–328, 1990.
7. Sambrook, et al., *Molecular Cloning: A Laboratory Manual*, Cold Spring Harbor Press, Cold Spring Harbor, 1989.
8. Xing, P. X., Tjandra, J. J., Stacker, S. A., Teh, J. G., Thompson, C. H., McLaughlin, P. J., and McKenzie, I. F. C., Monoclonal antibodies reactive with mucin expressed in breast cancer, *Immunol.Cell Biol.*, 67:183–185, 1989.
9. Apostolopoulos, V., Xing, P. X., Trapani, J. A. and McKenzie, I. F. C., Production of anti-breast cancer monoclonal antibodies using a glutathione-S-transferase-MUC1 bacterial fusion protein, *Br. J. Cancer*, 67:713–720, 1993.
10. Siddiqui, J., Abe, M., Hayes, D., Shani, E., Yunis, E. & Kufe, D., Isolation and sequencing of a cDNA coding for the human DF3 breast carcinoma-associated antigen, *Proc. Natl. Acad. Sci.*, 85:2320–2323, 1988.
11. Smith, D. B. & Johnson, K. S., Single-step purification of polypeptides expressed in *Escherichia coil* as fusions with glutathione S-transferase, *Gene*, 67:31–40, 1988.
12. Tomonari, K. A rat antibody against a structure functionally related to the mouse Tcell eceptoe/T3 complex, *Immunogenetics*, 28:455–458, 1988.
13. Pierres, A., Naquet, P., Van Agthoven, A., Bekkhoucha, F., Denizot, F., Mishal, Z., Schmitt-Verhulst, A-M. and Pierres, M., A rat anti-mouse T4 monoclonal antibody (H129.19) inhibits the proliferation of Ia-reactive T-cell clones and delineates two phenotypically distinct (T4+, Lyt-2,3-, and T4-, Lyt-2,3+) subsets among anti-Ia cytolytic T-cell clones, *J. Immunol.*, 132:2775–2782, 1984.
14. Ledbetter, J. A. and Herzenberg, L. A., Xenogeneic monoclonal antibodies to mouse lymphoid differentiation antigens, *Immunol., Rev.*, 47:63–90, 1979.
15. Harlow, D. and Lane, D., *A Laboratory Manual*, E. Harlow and D. Lane eds. Cold Spring Harbor Laboratory Press, Cold Spring Harbor, N.Y., 271, 1988.
16. Apostolopoulos, V., Xing, P. X., Trapani, J. A. and McKenzie, I. F. C., Production of anti-breast cancer 16. monoclonal antibodies using a glutathione-S-transferase-MUC1 bacterial fusion protein, *Br. J. Cancer,* 67(4):713–720, 1993.
17. Xing, P. X., Tjandra, J. J., Stacker, S. A., Teh, J. G., Thompson, C. H., McLaughlin, P. J., and McKenzie, I. F. C., Monoclonal antibodies reactive with mucin expressed in breast cancer, *Immunol.Cell Biol.,* 67:183–185, 1989.
18. Devine, P. L., Clark, B. A., Birrell, G. W., Layton, G. T., Ward, B. G, Alewood, P. F. and McKenzie, I. F. C., The breast tumor-associated epitope defined by monoclonal antibody 3E1.2 is an O-linked mucin carbohydrate containing N-glycolylneuramic acid, *Cancer Res.,* 51:5826–5836, 1991.
19. Hareuveni, M., Gautier, C., Kieny, M. P., Wreschner, D., Chambon, P. and Lathe, R., Vaccination against tumor cells expressing breast cancer epithelial tumor antigen, *Proc. Natl. Acad. Sci. USA,* 87:9498–9502, 1990.
20. Pierres, A., Naquet, P., VanAgthoven, A., Bekkhoucha, F., Denizot, F., Mishal, Z., Schmitt-Verhulst, A-M. and Pierres, M., A rat anti-mouse T4 monoclonal antibody (H129.19) inhibits the proliferation of Ia-reactive T-cell clones and delineates two phenotypically distinct (T4$^+$, Lyt-2,3-, and T4-, Lyt-2,3$^+$) subsets among anti-Ia cytolytic T-cell clones, *J. Immunol.,* 132:2775–2782, 1984.
21. Miller, R. A. and Stutman, O., Monoclonal antibody to Lyt 2 antigen blocks H-2I- and H-2K- specific mouse cytotoxic T-cells, *Nature,* 296:76–78, 1982.
22. Tomonari, K., A rat antibody against a structure functionally related to the mouse T-cell receptor/T3 complex, *Immunogenetics,* 28:455–458, 1988.
23. Auchincloss, H., Moses, R., Conti, D., Sundt, T., Smith, C., Sachs, D. H. and Winn, H. J., Rejection of transgenic skin expressing a xeno-classI antigen is CD4-dependent and CD8-independent, *Transpl. Proc.,* 22(3):1059–1060, 1990.
24. Pierres, A., Naquet, P., Van Agthoven, A., Bekkhoucha, F., Denizot, F., Mishal, Z., Schmitt-Verhulst, A-M. and Pierres, M., A rat anti-mouse T4 monoclonal antibody (H129.19) inhibits the proliferation of Ia-reactive T-cell clones and delineates two phenotypically distinct (T4+, Lyt-2,3-, and T4-, Lyt-2,3+) subsets among anti-Ia cytolytic T-cell clones, *J. Immunol.,* 132:2775–2782, 1984.
25. Ledbetter, J. A. and Herzenberg, L. A., Xenogeneic monoclonal antibodies to mouse lymiphoid differentiation antigens, *Immunol. Rev.,* 47:63–90, 1979.
26. Apostolopoulos, V., Xing, P. X., and McKenzie I. F. C., New Trends in the Development of a Breast Cancer Vaccine, *Cancer Forum,* 17:11–116, 1993.
27. Bobek, L. A., Tsai, H., Besbrock A. R., Levine, M. J, Molecular Cloning Sequence and Specificity of Expression of the Gene Encoding the Low Molecular Weight Human Salivary Mucin (MUC7), *J. Biol. Chem.,* 268:20563–20569, 1993.
28. Mandelboimo, O., Berke G., Fridkin, M., Feldman, M., Eisenstein, M., and Eisenbach, L., CTL Induction by a Tumour-associated Antigen Octapeptide Derived from a Murine Lung Carcinoma, *Nature,* 369,67–71, 1994.

What is claimed is:

1. A vaccine directed against tumour cells expressing human mucin or a subunit thereof which comprises a conjugate consisting essentially of a human mucin polypeptide or a variable number of tandem repeats thereof and oxidized mannan wherein oxidation generates aldehydes and conjugation generates Schiff bases, in association with a pharmaceutically acceptable carrier.

2. A vaccine according to claim 1, wherein said polypeptide comprises two to eighty copies as the variable number of tandem repeats of human mucin.

3. A vaccine according to claim 1, wherein said variable number of tandem repeats of said mucin polypeptide comprise part of a fusion protein.

4. A vaccine according to claim 2, wherein said variable number of tandem repeats of said mucin polypeptide comprise part of a fusion protein.

5. A vaccine according to claim 1, wherein said human mucin is MUC1.

6. A vaccine according to claim 2, wherein said human mucin is MUC1.

7. A vaccine according to claim 3, wherein said human mucin is MUC1.

8. A vaccine according to claim 4, wherein said human mucin is MUC1.

9. A vaccine as claimed in claim 3, wherein said fusion protein comprises a variable number of tandem repeats of said mucin polypeptide and a protein selected from the group consisting of glutathione-S-transferase and β galactosidase.

10. A vaccine as claimed in claim 4, wherein said fusion protein comprises a variable number of tandem repeats of said mucin polypeptide and a protein selected from the group consisting of glutathione-S-transferase and β galactosidase.

11. A method for inducing a cell-mediated immune response against a human mucin polypeptide antigen, said method comprising administering to an animal a conjugate consisting essentially of a human mucin polypeptide or a variable number of tandem repeats of said polypeptide and oxidized mannan, wherein oxidation generates aldehydes and conjugation generates Schiff bases, said conjugate being optionally combined with a pharmaceutically acceptable carrier.

12. The method of claim 11, wherein said conjugate comprises from two to eighty copies as the variable number of tandem repeats of said human mucin polypeptide.

13. The method according to claim 12, wherein said variable number of tandem repeats of human mucin polypeptide comprise part of a fusion polypeptide.

14. The method of claim 11, wherein said human mucin polypeptide is MUC1.

15. The method of claim 13, wherein said human mucin polypeptide is MUC1.

16. The method of claim 11, wherein said human mucin polypeptide antigen is associated with whole cells or subcellular fractions thereof.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 20 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Ser Ala Pro Asp Thr Arg Pro Ala Pro Gly Ser Thr Ala Pro Pro Ala
1           5                  10               15

His Gly Val Thr
       20

(2) INFORMATION FOR SEQ ID NO:2:

(i) SEQUENCE CHARACTERISTICS:
      (A) LENGTH: 23 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:2:

```
Pro Thr Thr Thr Pro Ile Ser Thr Thr Thr Met Val Thr Pro Thr Pro
1               5                   10                  15

Thr Pro Thr Gly Thr Gln Thr
            20
```

(2) INFORMATION FOR SEQ ID NO:3:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
His Ser Thr Pro Ser Phe Thr Ser Ser Ile Thr Thr Thr Glu Thr Thr
1               5                   10                  15

Ser
```

(2) INFORMATION FOR SEQ ID NO:4:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Thr Ser Ser Ala Ser Thr Gly His Ala Thr Pro Leu Pro Val Thr Asp
1               5                   10                  15
```

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Pro Thr Thr Ser Thr Thr Ser Ala
1               5
```

(2) INFORMATION FOR SEQ ID NO:6:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Thr Thr Ala Ala Pro Pro Thr Pro Pro Ala Thr Thr Pro Ala Pro Pro
1               5                   10                  15

Ser Ser Ser Ala Pro Pro Glu
            20
```

(2) INFORMATION FOR SEQ ID NO:7:

(i) SEQUENCE CHARACTERISTICS:

(A) LENGTH: 21 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Cys Pro Ala His Gly Val Thr Ser Ala Pro Asp Thr Arg Pro Ala Pro
1               5                   10                  15

Gly Ser Thr Ala Pro
            20

(2) INFORMATION FOR SEQ ID NO:8:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Pro Ala His Gly Val Thr Ser Ala Pro Asp Thr Arg Pro Ala Pro Gly
1               5                   10                  15

Ser Thr Ala Pro
            20

(2) INFORMATION FOR SEQ ID NO:9:

(i) SEQUENCE CHARACTERISTICS:
            (A) LENGTH: 25 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Thr Gly Ser Gly His Ala Ser Ser Thr Pro Gly Gly Glu Lys Glu Thr
1               5                   10                  15

Ser Ala Thr Gln Arg Ser Ser Val Pro
            20                  25

(2) INFORMATION FOR SEQ ID NO:10:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Arg Ser Ser Val Pro Ser Ser Thr Glu Lys Asn Ala Val Ser Met Thr
1               5                   10                  15

Ser Ser Val Leu
            20

(2) INFORMATION FOR SEQ ID NO:11:

(i) SEQUENCE CHARACTERISTICS:
            (A) LENGTH: 21 amino acids
            (B) TYPE: amino acid
            (C) STRANDEDNESS:

(D) TOPOLOGY: linear (ii) MOLECULE TYPE: peptide (xi) SEQUENCE DESCRIPTION: SEQ ID NO:11:

Asn Ser Ser Leu Glu Asp Pro Ser Thr Asp Val Val Gln Glu Leu Gln
1               5                   10                  15
Arg Asp Ile Ser Glu
            20

(2) INFORMATION FOR SEQ ID NO:12:

(i) SEQUENCE CHARACTERISTICS:
          (A) LENGTH: 16 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:12:

Thr Gly Phe Asn Gln Tyr Lys Thr Glu Ala Ala Ser Arg Val Asn Leu
1               5                   10                  15

(2) INFORMATION FOR SEQ ID NO:13:

(i) SEQUENCE CHARACTERISTICS:
          (A) LENGTH: 18 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:13:

Lys Thr Leu Val Leu Gly Lys Glu Gln Glu Ser Ala Glu Leu Pro Cys
1               5                   10                  15
Glu Tyr (2) INFORMATION FOR SEQ ID NO:14:

(i) SEQUENCE CHARACTERISTICS:
          (A) LENGTH: 21 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:14:

Pro Asp Thr Arg Pro Ala Pro Gly Ser Thr Ala Pro Pro Ala His Gly
1               5                   10                  15
Val Thr Ser Ala Pro
            20